US012807587B2

(12) United States Patent
Fawaz et al.

(10) Patent No.: US 12,807,587 B2
(45) Date of Patent: Nov. 24, 2026

(54) SYNTHESIS OF MDA OR ITS OPTICALLY ACTIVE (R)- OR (S)-MDA ISOMERS

(71) Applicant: EMPATHBIO, INC., Encinitas, CA (US)

(72) Inventors: Majed Fawaz, Foxborough, MA (US); Nicholas Morra, Ontario (CA)

(73) Assignee: EmpathBio, Inc., New York, NY (US)

( * ) Notice: Subject to any disclaimer, the term of this patent is extended or adjusted under 35 U.S.C. 154(b) by 400 days.

(21) Appl. No.: 18/504,848

(22) Filed: Nov. 8, 2023

(65) Prior Publication Data

US 2024/0208920 A1 Jun. 27, 2024

Related U.S. Application Data

(60) Provisional application No. 63/423,597, filed on Nov. 8, 2022.

(51) Int. Cl.
*C07D 317/58* (2006.01)

(52) U.S. Cl.
CPC .................................. *C07D 317/58* (2013.01)

(58) Field of Classification Search
CPC .................................................... C07D 317/58
USPC .......................................................... 549/440
See application file for complete search history.

(56) References Cited

U.S. PATENT DOCUMENTS

| | | | |
|---|---|---|---|
| 3,907,864 | A | 9/1975 | Biel et al. |
| 4,017,636 | A | 4/1977 | Jones et al. |
| 4,937,360 | A | 6/1990 | Liu et al. |
| 5,061,727 | A | 10/1991 | Bloom et al. |
| 5,861,426 | A | 1/1999 | Del Soldato et al. |
| 5,932,749 | A | 8/1999 | Li et al. |
| 6,436,950 | B1 | 8/2002 | Achari et al. |
| 7,048,545 | B2 | 5/2006 | McClusky |
| 9,878,992 | B2 | 1/2018 | Bhamidipati et al. |
| 9,907,812 | B2 | 3/2018 | Bapat et al. |
| 10,000,555 | B2 | 6/2018 | Doronina et al. |
| 11,414,423 | B1 | 8/2022 | Olson et al. |
| 11,845,736 | B2 | 12/2023 | Rao et al. |
| 11,912,680 | B2 | 2/2024 | Perni et al. |
| 11,958,821 | B2 | 4/2024 | Clark |
| 11,993,577 | B2 | 5/2024 | Fawaz et al. |
| 12,221,428 | B2 | 2/2025 | Cozzi et al. |
| 12,365,661 | B2 | 7/2025 | Baggott |
| 12,454,516 | B2 | 10/2025 | Perni |
| 12,492,178 | B2 | 12/2025 | Fawaz et al. |
| 2003/0171303 | A1 | 9/2003 | Gallop et al. |
| 2003/0207884 | A1 | 11/2003 | Haap et al. |
| 2005/0130244 | A1 | 6/2005 | Zheng et al. |
| 2006/0035863 | A1 | 2/2006 | Barbeau |
| 2006/0205779 | A1 | 9/2006 | Mu et al. |
| 2006/0205946 | A1 | 9/2006 | Ji et al. |
| 2007/0027208 | A1 | 2/2007 | Caron et al. |
| 2008/0045588 | A1 | 2/2008 | Gant et al. |
| 2008/0146567 | A1 | 6/2008 | Kolczewski et al. |
| 2008/0293695 | A1 | 11/2008 | Bristol et al. |
| 2009/0111741 | A1 | 4/2009 | Aldrich et al. |
| 2009/0131516 | A1 | 5/2009 | Mickle et al. |
| 2009/0143408 | A1 | 6/2009 | Eissenstat et al. |
| 2010/0137428 | A1 | 6/2010 | Bozzoli et al. |
| 2013/0317020 | A1 | 11/2013 | Ruah et al. |
| 2014/0243544 | A1 | 8/2014 | Wang et al. |
| 2018/0243241 | A1 | 8/2018 | Popp et al. |
| 2018/0344728 | A1 | 12/2018 | Bosse et al. |
| 2020/0369707 | A1 | 11/2020 | Verhoeven et al. |
| 2021/0113559 | A1 | 4/2021 | Boss et al. |
| 2021/0145851 | A1 | 5/2021 | Stamets |
| 2021/0332012 | A1 | 10/2021 | Olson et al. |
| 2021/0346341 | A1 | 11/2021 | Liechti |
| 2022/0151986 | A1 | 5/2022 | Liechti et al. |
| 2022/0267252 | A1 | 8/2022 | Trachsel et al. |
| 2022/0354822 | A1 | 11/2022 | Barrow et al. |
| 2023/0096116 | A1 | 3/2023 | Fawaz et al. |
| 2023/0097530 | A1 | 3/2023 | Short et al. |
| 2023/0109467 | A1 | 4/2023 | Anzalone et al. |
| 2023/0113351 | A1 | 4/2023 | Blumstock et al. |
| 2023/0129723 | A1 | 4/2023 | Short et al. |
| 2023/0150965 | A1 | 5/2023 | Duncton et al. |
| 2023/0150966 | A1 | 5/2023 | Duncton et al. |
| 2023/0181521 | A1 | 6/2023 | Duncton et al. |
| 2023/0202998 | A1 | 6/2023 | Duncton et al. |
| 2023/0227420 | A1 | 7/2023 | Rao et al. |

(Continued)

FOREIGN PATENT DOCUMENTS

| | | | |
|---|---|---|---|
| AU | 2018268311 | B2 | 2/2022 |
| CN | 101822841 | A | 9/2010 |

(Continued)

OTHER PUBLICATIONS

Australian and New Zealand Clinical Trials Registry, Identifier ACTRN12622001335785. "A Phase 1 Randomized, First-in-Human, Double-Blind, Placebo-Controlled Study to Evaluate the Safety, Tolerability, Pharmacokinetics, and Pharmacodynamics of Single-Ascending Doses of EMP-01 in Healthy Adult Volunteers." [Internet]: Sydney (NSW): NHMRC Clinical Trials Centre, University of Sydney Australia; (Oct. 18, 2022), last updated Feb. 14, 2024 [retrieved from the Internet Oct. 23, 2025, from https://www.anzctr.org.au/Trial/Registration/TrialReview.aspx?id=384394&isReview=true]; 7 pages.

EP Application No. 22865560.1, Extended European Search Report mailed Jul. 28, 2025; Applicant EmpathBio, Inc.; 6 pages.

EP Application No. 22877438.6, Extended European Search Report mailed Sep. 30, 2025; Applicant EmpathBio, Inc.; 8 pages.

Ozber N., et al., "Bioproduction of 3,4-methylenedioxymethamphetamine and derivatives." BioDesign Research, Jun. 2025, vol. 7, Issue 2, 100011, 11 pages.

Shulgin, A. T., "The Background and Chemistry of MDMA." J Psychoactive Drugs. Oct.-Dec. 1986;18(4):291-304. doi: 10.1080/02791072.1986.10472361.

U.S. Appl. No. 19/366,168, filed Oct. 22, 2025; Inventor Fawaz, Majed et al.

(Continued)

*Primary Examiner* — Kahsay Habte
(74) *Attorney, Agent, or Firm* — COOLEY LLP

(57) ABSTRACT

Provided herein is a process for the preparation of 3,4-methylenedioxyamphetamine, (R)-3,4-methylenedioxyamphetamine and (S)-3,4-methylenedioxyamphetamine.

20 Claims, No Drawings

(56) References Cited

U.S. PATENT DOCUMENTS

| | | | |
|---|---|---|---|
| 2023/0227421 | A1 | 7/2023 | Perni et al. |
| 2023/0227422 | A1 | 7/2023 | Duncton et al. |
| 2023/0278977 | A1 | 9/2023 | Fawaz et al. |
| 2023/0310368 | A1 | 10/2023 | Barrow et al. |
| 2023/0416219 | A1 | 12/2023 | Schneider et al. |
| 2024/0082212 | A1 | 3/2024 | Short et al. |
| 2024/0217944 | A1 | 7/2024 | Fawaz |
| 2024/0285577 | A1 | 8/2024 | Nair et al. |
| 2024/0327371 | A1 | 10/2024 | Clark |
| 2024/0335418 | A1 | 10/2024 | Obidin et al. |
| 2024/0342126 | A1 | 10/2024 | Slassi et al. |
| 2024/0400532 | A1 | 12/2024 | Perni |
| 2024/0408054 | A1 | 12/2024 | Short et al. |
| 2024/0409526 | A1 | 12/2024 | Clark |
| 2024/0425470 | A1 | 12/2024 | Khan et al. |
| 2025/0026731 | A1 | 1/2025 | Rao et al. |
| 2025/0034105 | A1 | 1/2025 | Duncton et al. |
| 2025/0152553 | A1 | 5/2025 | Khan et al. |
| 2025/0205191 | A1 | 6/2025 | Rao et al. |
| 2026/0028324 | A1 | 1/2026 | Perni et al. |
| 2026/0055075 | A1 | 2/2026 | Fawaz et al. |
| 2026/0132118 | A1 | 5/2026 | Fawaz et al. |

FOREIGN PATENT DOCUMENTS

| | | | |
|---|---|---|---|
| CN | 110294789 | A | 10/2019 |
| DK | 3271357 | T3 | 2/2020 |
| EP | 2687854 | A1 | 1/2014 |
| NZ | 239929 | A | 12/1994 |
| WO | WO-2004004648 | A2 | 1/2004 |
| WO | WO-2005019163 | A2 | 3/2005 |
| WO | WO-2005038049 | A2 | 4/2005 |
| WO | WO-2007090733 | A1 | 8/2007 |
| WO | WO-2008033351 | A2 | 3/2008 |
| WO | WO-2008046135 | A1 | 4/2008 |
| WO | WO-2009049233 | A1 | 4/2009 |
| WO | WO-2009089494 | A2 | 7/2009 |
| WO | WO-2009095479 | A2 | 8/2009 |
| WO | WO-2012177986 | A2 | 12/2012 |
| WO | WO-2013088255 | A1 | 6/2013 |
| WO | WO-2014013063 | A1 | 1/2014 |
| WO | WO-2014139161 | A1 | 9/2014 |
| WO | WO-2016148306 | A1 | 9/2016 |
| WO | WO-2017147375 | A1 | 8/2017 |
| WO | WO-2018210988 | A1 | 11/2018 |
| WO | WO-2019018584 | A1 | 1/2019 |
| WO | WO-2020077217 | A1 | 4/2020 |
| WO | WO-2020101543 | A1 | 5/2020 |
| WO | WO-2020252384 | A1 | 12/2020 |
| WO | WO-2021252538 | A2 | 12/2021 |
| WO | WO-2022006192 | A1 | 1/2022 |
| WO | WO-2022010937 | A1 | 1/2022 |
| WO | WO-2022032147 | A1 | 2/2022 |
| WO | WO-2022053696 | A1 | 3/2022 |
| WO | WO-2022061242 | A1 | 3/2022 |
| WO | WO-2022069690 | A2 | 4/2022 |
| WO | WO-2022106947 | A1 | 5/2022 |
| WO | WO-2022150525 | A1 | 7/2022 |
| WO | WO-2022182602 | A2 | 9/2022 |
| WO | WO-2022232948 | A1 | 11/2022 |
| WO | WO-2022235530 | A1 | 11/2022 |
| WO | WO-2022251690 | A1 | 12/2022 |
| WO | WO-2022256720 | A2 | 12/2022 |
| WO | WO-2023283373 | A1 | 1/2023 |
| WO | WO-2023283386 | A2 | 1/2023 |
| WO | WO-2023019369 | A1 | 2/2023 |
| WO | WO-2023034510 | A1 | 3/2023 |
| WO | WO-2023044027 | A1 | 3/2023 |
| WO | WO-2023056102 | A1 | 4/2023 |
| WO | WO-2023056472 | A1 | 4/2023 |
| WO | WO-2023081895 | A1 | 5/2023 |
| WO | WO-2023081897 | A1 | 5/2023 |
| WO | WO-2023081899 | A1 | 5/2023 |
| WO | WO-2023092044 | A2 | 5/2023 |
| WO | WO-2023129958 | A2 | 7/2023 |
| WO | WO-2023131841 | A1 | 7/2023 |
| WO | WO-2023250247 | A2 | 12/2023 |
| WO | WO-2024052880 | A1 | 3/2024 |
| WO | WO-2024054279 | A1 | 3/2024 |
| WO | WO-2024102845 | A2 | 5/2024 |
| WO | WO-2024145663 | A2 | 7/2024 |
| WO | WO-2024148267 | A1 | 7/2024 |
| WO | WO-2024166057 | A1 | 8/2024 |
| WO | WO-2024166058 | A1 | 8/2024 |
| WO | WO-2024166059 | A1 | 8/2024 |
| WO | WO-2024254411 | A2 | 12/2024 |
| WO | WO-2024254505 | A2 | 12/2024 |
| WO | WO-2025010308 | A2 | 1/2025 |
| WO | WO-2025096895 | A1 | 5/2025 |
| WO | WO-2025137563 | A1 | 6/2025 |

OTHER PUBLICATIONS

U.S. Appl. No. 19/345,242, filed Sep. 30, 2025; Inventor Perni et al.

Acquas et al., "Differential effects of intravenous R, S-(±)-3, 4-methylenedioxymethamphetamine (MDMA, Ecstasy) and its S (+)-and R (−)-enantiomers on dopamine transmission and extracellular signal regulated kinase phosphorylation (pERK) in the rat nucleus accumbens shell and core." Journal of Neurochemistry (2007); 102(1): 121-132. doi: 10.1111/j.1471-4159.2007.04451.x.

Alexander, J., et al., "(Acyloxy)alkyl carbamates as novel bioreversible prodrugs for amines: increased permeation through biological membranes." J Med Chem. Feb. 1988;31(2):318-22. doi: 10.1021/jm00397a008.

Anderson et al., "Absolute configuration and psychotomimetic activity", 'QuaSAR' Research Monograph, National Institute on Drug Abuse (1978); 22: 8-15.

Angerer et al., "Acute psychotropic, autonomic, and endocrine effects of 5,6-methylenedioxy-2-aminoindane (MDAI) compared with 3,4-methylenedioxymethamphetamine (MDMA) in human volunteers: A self-administration study." Drug Test Anal. Sep. 2024; 16(9):1002-1011. doi: 10.1002/dta.3622. Epub Dec. 6, 2023.

Auvelity, (dextromethorphan HBr and bupropion HCl) extended-release tablets, Prescribing Information, Axsome Therapeutics, Inc., 2022. 19 pages.

Baker et al., "Critical evaluation of methodology commonly used in sample collection, storage and preparation for the analysis of pharmaceuticals and illicit drugs in surface water and wastewater by solid phase extraction and liquid chromatography-mass spectrometry." J Chromatogr A. Nov. 4, 2011;1218(44):8036-59. doi: 10.1016/j.chroma.2011.09.012. Epub Sep. 10, 2011, 61 pages.

Baker, et al., "Drugs of abuse in wastewater and suspended particulate matter—Further developments in sewage epidemiology." Environ Int. Nov. 1, 2012: 48: 28-38. doi: 10.1016/j.envint.2012.06.014. Epub Jul. 24, 2012.

Baker et al., "Multi-residue analysis of drugs of abuse in wastewater and surface water by solid-phase extraction and liquid chromatography-positive electrospray ionisation tandem mass spectrometry." J Chromatogr A. Mar. 25, 2011;1218(12):1620-31. doi: 10.1016/j.chroma.2011.01.060. Epub Jan. 28, 2011.

Baker, et al., "Multi-residue determination of the sorption of illicit drugs and pharmaceuticals to wastewater suspended particulate matter using pressurized liquid extraction, solid phase extraction and liquid chromatography coupled with tandem mass spectrometry." J Chromatogr A. Nov. 4, 2011; 1218(44): 7901-13. doi: 10.1016/j.chroma.2011.08.092. Epub Sep. 8, 2011.

Barreiro, J.C., et al., "A High-Resolution Magic Angle Spinning NMR Study of the Enantiodiscrimination of 3,4-Methylenedioxymethamphetamine (MDMA) by an Immobilized Polysaccharide-Based Chiral Phase." PLoS One. Sep. 26, 2016; 11(9): e0162892. doi: 10.1371/journal.pone.0162892. eCollection 2016. 11pages.

Bartz, J., et al., "Oxytocin can hinder trust and cooperation in borderline personality disorder." Soc Cogn Affect Neurosci., Oct. 2011; 6(5): 556-63.

Battaglia et al., "Pharmacologic profile of MDMA (3,4-methylenedioxymethamphetamine) at various brain recognition sites." Eur J Pharmacol. Apr. 27, 1988; 149(1-2): 159-63. doi: 10.1016/0014-2999(88)90056-8.

(56) References Cited

OTHER PUBLICATIONS

Baumann et al., "Effects of dose and route of administration on pharmacokinetics of (+ or −)-3,4-methylenedioxymethamphetamine in the rat." Drug Metab Dispos. Nov. 2009; 37(11): 2163-70. doi: 10.1124/dmd.109.028506. Epub Aug. 13, 2009.
Berge et al., "Pharmaceutical salts," Journal of Pharmaceutical Sciences 66(1):1-19 (Jan. 1977).
Biezonski et al., "Effects of a short-course MDMA binge on dopamine transporter binding and on levels of dopamine and its metabolites in adult male rats." Eur J Pharmacol. Feb. 15, 2013; 701(1-3): 176-80. doi: 10.1016/j.ejphar.2012.12.024. Epub Dec. 28, 2012.
Blanchard et al., "Ethoexperimental approaches to the biology of emotion." Annu Rev Psychol. 1988: 39: 43-68. doi: 10.1146/annurev.ps.39.020188.000355.
Bobes, J., "How is recovery from social anxiety disorder defined?" The Journal of Clinical Psychiatry. J Clin Psychiatry. 1998: 59 Suppl 17:12-19.
Brooks et al., "The significance of chirality in drug design and development." Curr Top Med Chem. 2011;11(7):760-70. doi: 10.2174/156802611795165098.
Brøsen, K., et al., "Extensive Metabolizers of Debrisoquine Become Poor Metabolizers during Quinidine Treatment." Pharmacol Toxicol. Apr. 1987; 60(4): 312-4. doi: 10.1111/j.1600-0773.1987.tb01758.x.
Buttonwood, "Single crystal x-ray diffraction experiment backwards: from CIF to genuine set of raw data without performing actual experiment." Chemistry Stack Exchange, 6 pages, Jun. 28, 2017. URL:https://chemistry.stackexchange.com/questions/76950/singlecrystal-x-ray-diffraction-experiment-backwards-from-cif-to-genuine-set?.
Cambridge Crystallographic Data Centre, CSD Entry: BEQRUN, 2 pages, Deposited Feb. 23, 2018, retrieved Jul. 22, 2025, https://www.ccdc.cam.ac.uk/structures/Search?Ccdcid=BEQRUN&DatabasToSearch=Published.
Carbonaro, T. et al., "Double-blind comparison of the two hallucinogens psilocybin and dextromethorphan: similarities and differences in subjective experiences." Psychopharmacology (Berl). Feb. 2018; 235(2): 521-534. doi: 10.1007/s00213-017-4769-4. Epub Nov. 7, 2017.
Carhart-Harris et al., "Trial of psilocybin versus escitalopram for depression", New England Journal of Medicine (2021); 384(15): 1402-1411. doi: 10.1056/NEJMoa2032994.
Carhart-Harris, "Psilocybin for treatment-resistant depression: fMRI-measured brain mechanisms." Sci Rep. Oct. 13, 2017; 7(1): 13187. doi: 10.1038/s41598-017-13282-7. 11 pages.
Cascorbi, I., "Pharmacogenetics of cytochrome P4502D6: genetic background and clinical implication." Eur J Clin Invest. Nov. 2003: 33 (Suppl 2): 17-22. doi: 10.1046/j.1365-2362.33.s2.3.x.
Castrignano, et al., "Enantiomeric profiling of chiral drug biomarkers in wastewater with the usage of chiral liquid chromatography coupled with tandem mass spectrometry." J Chromatogr A. Mar. 18, 2016:1438:84-99. doi: 10.1016/j.chroma.2016.02.015. Epub Feb. 6, 2016.
Castrignano, et al., Enantiomeric profiling of chiral illicit drugs in a pan-European study, Water Res. Mar. 1, 2018: 130: 151-160. doi: 10.1016/j.watres.2017.11.051. Epub Dec. 1, 2017.
Challener, C. A, "Chiral Resolution with and without Resolving Agents." Pharmaceutical Technology, vol. 39, Issue 2, Feb. 2, 2015, 9 pages.
Chaly and Diksic, "High yield synthesis of 6-[18F]fluoro-L-dopa by regioselective fluorination of protected L-dopa with [18F]acetylhypofluorite." J Nucl Med. Dec. 1986; 27(12): 1896-901.
Chen et al., "Investigation of the relationship between phenol ionization and affinity of norepinephrine for adrenergic receptors using ring-fluorinated analogs." Medicinal Chemistry Research, 1993, 3(9) pp. 589-597.
Chen, et al., "Syntheses of 2,5- and 2,6-difluoronorepinephrine, 2,5-difluoroepinephrine, and 2,6-difluorophenylephrine: effect of disubstitution with fluorine on adrenergic activity." J Med Chem. Nov. 26, 1993; 36(24): 3947-55. doi: 10.1021/jm00076a024.
Clinical Trials.gov., ID NCT03537014, "A Multi-site Phase 3 study of MDMA-Assisted Psychotherapy for PTSD (MAPP1)." National Library of Medicine, Sponsor Lykos Therapeutics, ((Aug. 18, 2021) Study Record Version 46) (Year: 2021), 32 pages.
ClinicalTrials.gov ID NCT05277636, "Acute Effects of R- and S-MDMA in Healthy Subjects (R-S-MDMA)." National Library of Medicine, Sponsor University Hospital, Basel, Switzerland, Study start, Oct. 1, 2022, 13 pages.
Clouting, H., "The Commercial Chemistry of MDMA: From Research to Patient Access," MAPS Bulletin Special Edition, Spring 2020, pp. 8-10.
Cohen, I., et al., "Concomitant drugs associated with increased mortality for MDMA users reported in a drug safety surveillance database." Scientific Reports, (2021) 11: 5997, 9 pages.
Collins et al., "Identification and characterization of N-tert-butoxycarbonyl-MDMA: a new MDMA precursor", Drug Testing and Analysis (Mar. 2017); 9(3): 399-404. doi: 10.1002/dta.2059. Epub Sep. 29, 2016.
Connarn et al., "Pharmacokinetics and Pharmacogenomics of Bupropion in Three Different Formulations with Different Release Kinetics in Healthy Human Volunteers." AAPS J. Sep. 2017; 19(5): 1513-1522. doi: 10.1208/s12248-017-0102-8. Epub Jul. 6, 2017.
Corkery et al., "Deaths in the Lesbian, Gay, Bisexual and Transgender United Kingdom Communities Associated with GHB and Precursors." Curr Drug Metab. 2018; 19(13): 1086-1099. doi: 10.2174/1389200218666171108163817.
Crean, et al., "Oral Administration of (±)3,4-Methylenedioxymethamphetamine and (+) Methamphetamine Alters Temperature and Activity in Rhesus Macaques." Pharmacol Biochem Behav. May 2007;87(1):11-9. doi: 10.1016/j.pbb.2007.03.015. Epub Apr. 3, 2007.
Crisp et al., "The antinociceptive effects of 3, 4-methylenedioxymethamphetamine (MDMA) in the rat", Pharmacology Biochemistry and Behavior (1989); 34(3): 497-501. doi: 10.1016/0091-3057(89)90547-9.
Curry et al. "Separating the agony from ecstasy: R (−)-3, 4-methylenedioxymethamphetamine has prosocial and therapeutic-like effects without signs of neurotoxicity in mice." Neuropharmacology. Jan. 2018;128:196-206.
Dalgleish, T., et al., "Transdiagnostic Approaches to Mental Health Problems: Current Status and Future Directions." Journal of Consulting and Clinical Psychology, 2020, vol. 88, No. 3, 179-195.
Danforth et al., "Reduction in social anxiety after MDMA-assisted psychotherapy with autistic adults: a randomized, double-blind, placebo-controlled pilot study", Psychopharmacology (Nov. 2018); 235(11): 3137-3148. doi: 10.1007/s00213-018-5010-9. Epub Sep. 8, 2018.
De La Torre and Farre, "Neurotoxicity of MDMA (ecstasy): the limitations of scaling from animals to humans." Trends Pharmacol Sci. Oct. 2004;25(10):505-8. doi: 10.1016/j.tips.2004.08.001., 4 pages.
De La Torre et al., "MDMA, methamphetamine, and CYP2D6 pharmacogenetics: what is clinically relevant?", Frontiers in Genetics (2012); 3: 235; 8 pages .doi: 10.3389/fgene.2012.00235.
De La Torre et al., "Non-linear pharmacokinetics of MDMA ('ecstasy') in humans." Br J Clin Pharmacol. Feb. 2000; 49(2): 104-9. doi: 10.1046/j.1365-2125.2000.00121.x.
De Vos et al., "Psychedelics and Neuroplasticity: A Systematic Review Unraveling the Biological Underpinnings of Psychedelics." Front Psychiatry. Sep. 10, 2021: 12: 724606. doi: 10.3389/fpsyt.2021.724606. eCollection 2021.17 pages.
Deluca et al., "Searching the Internet for drug-related web sites: analysis of online available information on ecstasy (MDMA)." Am J Addict. Nov.-Dec. 2007;16(6):479-83. doi: 10.1080/10550490701641181.
Doly et al., "Role of Serotonin via 5-HT2B Receptors in the Reinforcing Effects of MDMA in Mice." PLoS One. Nov. 23, 2009; 4(11): e7952. doi: 10.1371/journal.pone.0007952. 10 pages.
Duman et al., "Synaptic plasticity and depression: new insights from stress and rapid-acting antidepressants." Nat Med. Mar. 2016; 22(3): 238-49. doi: 10.1038/nm.4050.

(56) References Cited

OTHER PUBLICATIONS

Dunlap et al., "Dark classics in chemical neuroscience: 3, 4-methylenedioxymethamphetamine", ACS Chemical Neuroscience (2018); 9(10): 2408-2427. doi: 10.1021/acschemneuro.8b00155. Epub Jul. 12, 2018.

Eiden, et al., "VMAT2: a dynamic regulator of brain monoaminergic neuronal function interacting with drugs of abuse." Ann N Y Acad Sci. Jan. 2011: 1216: 86-98. doi: 10.1111/j.1749-6632.2010.05906.x.

Ellinwood Jr. et al., "Fundamental mechanisms underlying altered behavior following chronic administration of psychomotor stimulants." Biological Psychiatry, Oct. 1, 1980, 15(5):749-757.

Erowid, "Like a Happy Smiley Speed MOMA, Escitalopram & Divalproex." May 29, 2021, Erowid.org Retrieved May 29, 2021. URL: https://www.erowid.org/experiences/exp.php?ID=89532. 6 pages.

Erowid, "Unexpectedly Hard Tripping . . . All Good, too." Jul. 7, 2021, Erowid, URL:https://www.erowid.org/experiences/exp.php?ID=108919. 3 pages.

Eurofins SafetyScreen87 Panel, Panlabs, available online at https://www.eurofinsdiscovery.com/catalog/safetyscreen87-panel-tw/PP223, date unknown, document copyright date 2023, 4 pages.

Extended European Search Report for European Application No. 22877644.9 mailed Jul. 11, 2025, 8 pages.

Fallon et al., "Stereospecific Analysis and Enantiomeric Disposition of 3,4-Methylenedioxymethamphetamine (Ecstasy) in Humans," Clinical Chemistry (1999) 45:7, 1058-1069.

Fantegrossi et al., "3, 4-Methylenedioxymethamphetamine (MDMA, "ecstasy") and its stereoisomers as reinforcers in rhesus monkeys: serotonergic involvement." Psychopharmacology (Berl). Jun. 2002;161(4):356-64. doi: 10.1007/s00213-002-1021-6. Epub Apr. 19, 2002.

Fantegrossi et al., "Serotonin synthesis inhibition reveals distinct mechanisms of action for MDMA and its enantiomers in the mouse", Psychopharmacology (2005); 181(3): 529-536. doi: 10.1007/s00213-005-0005-8. Epub Oct. 12, 2005.

Fantegrossi et al., "Nantenine: an antagonist of the behavioral and physiological effects of MDMA in mice." Psychopharmacology (2004) 173:270-277.

Fantegrossi et al., "Pharmacological characterization of the effects of 3, 4-methylenedioxymethamphetamine ("ecstasy") and its enantiomers on lethality, core temperature, and locomotor activity in singly housed and crowded mice", Psychopharmacology (2003); 166: 202-211. doi: 10.1007/s00213-002-1261-5. Epub Feb. 1, 2003.

Fantegrossi, "In vivo pharmacology of MDMA and its enantiomers in rhesus monkeys." Exp Clin Psychopharmacol. Feb. 2008; 16(1): 1-12. doi: 10.1037/1064-1297.16.1.1.

Feduccia, "MDMA-assisted psychotherapy for PTSD: Are memory reconsolidation and fear extinction underlying mechanisms?" Progress in Neuropsychopharmacology & Biological Psychiatry vol. 84, pp. 221-228, 2019.

Felim et al., "Synthesis and in Vitro Cytotoxicity Profile of the R-Enantiomer of 3,4-Dihydroxymethamphetamine (R-(−)-HHMA): Comparison with Related Catecholamines," Chem. Res. Toxicol. 2010, 23, 211-219.

Filler, R., "Fluorine-containing catecholamines. Synthesis of DL-2,5,6-trifluorodopa." Journal of fluorine chemistry, 1981, vol. 18(4), p. 483-495.

Fitzgerald et al., "Stereoselective pharmacokinetics of 3, 4-methylenedioxymethamphetamine in the rat." Chirality. 1990;2(4):241-8. doi: 10.1002/chir.530020409.

Forsling et al., "The effect of 3,4-methylenedioxymethamphetamine (MDMA,'ecstasy') and its metabolites on neurohypophysial hormone release from the isolated rat hypothalamus." British Journal of Pharmacology (2002); 135(3): 649-656. doi: 10.1038/sj.bjp.0704502.

Frith et al., "Toxicity of methylenedioxymethamphetamine (MDMA) in the dog and the rat." Fundam Appl Toxicol. Jul. 1987; 9(1): 110-9. doi: 10.1016/0272-0590(87)90158-8.

Gauvin et al., "Establishing performance characteristics for positive control article selection in drug self-administration studies." Journal of Pharmacological and Toxicological Methods vol. 97, May-Jun. 2019, pp. 13-23.

Glue et al., "Influence of CYP2D6 activity on the pharmacokinetics and pharmacodynamics of a single 20 mg dose of ibogaine in healthy volunteers." J Clin Pharmacol. Jun. 2015; 55(6): 680-7. doi: 10.1002/jcph.471. Epub Feb. 25, 2015.

Gold and Koob, "MDMA produces stimulant-like conditioned locomotor activity." Psychopharmacology (Berl). 1989; 99(3): 352-6. doi: 10.1007/BF00445556.

Gopisankar, M. G., "CYP2D6 pharmacogenomics." The Egyptian Journal of Medical Human Genetics 18 (2017) 309-313.

Green et al., "The pharmacology and clinical pharmacology of 3,4-methylenedioxymethamphetamine (MDMA, "ecstasy")", Pharmacol Rev, Sep. 2003; 55(3): 463-508. Epub Jul. 17, 2003.

Green, R., et al., "MDMA: on the translation from rodent to human dosing." Psychopharmacology (Berl). Jun. 2009; 204(2): 375-8. doi: 10.1007/s00213-008-1453-8. Epub Jan. 13, 2009.

Haberzettl et al., "Animal models of the serotonin syndrome: a systematic review." Behav Brain Res. Nov. 1, 2013: 256: 328-45. doi: 10.1016/j.bbr.2013.08.045. Epub Sep. 1, 2013.

Hagele et al., "Enantioselective separation of Novel Psychoactive Substances using a Lux® AMP 3 μm column and HPLC-UV." J Pharm Biomed Anal. Feb. 5, 2020:179:112967. doi: 10.1016/j.jpba.2019.112967. Epub Nov. 5, 2019. 2 pages.

Halberstadt and Geyer, "Characterization of the head-twitch response induced by hallucinogens in mice: detection of the behavior based on the dynamics of head movement," Psychopharmacology (Berl). Jun. 2013;227(4):727-39. doi: 10.1007/s00213-013-3006-z. Epub Feb. 14, 2013.

Halberstadt et al., "Correlation between the potency of hallucinogens in the mouse head-twitch response assay and their behavioral and subjective effects in other species." Neuropharmacology. May 1, 2020: 167: 107933. doi: 10.1016/j.neuropharm.2019.107933. Epub Jan. 7, 2020, 12 pages.

Han et al., "Comparison of the monoamine transporters from human and mouse in their sensitivities to psychostimulant drugs." BMC Pharmacol. Mar. 3, 2006: 6: 6. doi: 10.1186/1471-2210-6-6. 7 pages.

Heather, E., "The Synthesis and Chemical Profiling of 3,4-Methylenedioxymethamphetamine (MDMA) and Analogues," Thesis, University of Technology Sydney, Oct. 2020, 232 pages.

Hensley, et al., "Simultaneous determination of amphetamine, methamphetamine, methylenedioxyamphetamine (MDA), methylenedioxymethamphetamine (MDMA), and methylenedioxyethylamphetamine (MDEA) enantiomers by GC-MS." Journal of Analytical Toxicology, Oct. 1999, pp. 518-523.

Herr et al., "Re-evaluation of the discriminative stimulus effects of lysergic acid diethylamide with male and female Sprague-Dawley rats." Behav Pharmacol. Dec. 2020; 31(8): 776-786.

Heydari, A., et al., "Mechanism-based inactivation of CYP2D6 by methylenedioxymethamphetamine." Drug Metab Dispos. Nov. 2004; 32(11): 1213-7. doi: 10.1124/dmd.104.001180. Epub Aug. 24, 2004.

Hilaire et al., "The role of serotonin in respiratory function and dysfunction." Respiratory Physiology & Neurobiology vol. 174, Issues 1-2, Nov. 30, 2010, pp. 76-88.

Hiramatsu et al., "Enantiomeric differences in the effects of 3, 4-methylenedioxymethamphetamine on extracellular monoamines and metabolites in the striatum of freely-moving rats: an in vivo microdialysis study", Neuropharmacology (1990); 29(3): 269-275. doi: 10.1016/0028-3908(90)90012-g.

Holze et al., "Distinct acute effects of LSD, MDMA, and D-amphetamine in healthy subjects." Neuropsychopharmacology. Feb. 2020;45(3):462-471. doi: 10.1038/s41386-019-0569-3.

Huot et al., "Characterization of 3,4-Methylenedioxymethamphetamine (MDMA) Enantiomers In Vitro and in the MPTP-Lesioned Primate: R-MDMA Reduces Severity of Dyskinesia, Whereas S-MDMA Extends Duration of ON-Time", The Journal of Neuroscience (May 11, 2011); 31(19): 7190-7198. doi: 10.1523/JNEUROSCI.1171-11.2011.

(56) References Cited

OTHER PUBLICATIONS

Hysek et al., "The norepinephrine transporter inhibitor reboxetine reduces stimulant effects of MDMA ("ecstasy") in humans." Clinical Pharmacology & Therapeutics. Aug. 2011;90(2):246-255. doi: 10.1038/clpt.2011.78.
Hysek et al., "Duloxetine inhibits effects of MDMA ("ecstasy") in vitro and in humans in a randomized placebo-controlled laboratory study." PloS One. May 4, 2012;7(5):e36476; 15 pages. doi: 10.1371/journal.pone.0036476.
Hysek et al., "Effects of the α2-adrenergic agonist clonidine on the pharmacodynamics and pharmacokinetics of 3, 4-methylenedioxymethamphetamine in healthy volunteers." The Journal of Pharmacology and Experimental Therapeutics. Feb. 2012;340(2):286-294. doi: 10.1124/jpet.111.188425.
Hysek et al., "MDMA enhances emotional empathy and prosocial behavior." Social Cognitive and Affective Neuroscience. Nov. 2014;9(11):1645-1652. doi: 10.1093/scan/nst161.
Inouye et al., "MDMA-assisted therapy for borderline personality disorder." Journal of Psychedelic Studies, 7 (2023) 3, 227-237, DOI:10.1556/2054.2023.00196.
International Preliminary Report on Patentability for International Application No. PCT/IB2023/058939 mailed Mar. 20, 2025, 8 pages.
International Preliminary Report on Patentability for International Application No. PCT/US2022/042353 dated Nov. 7, 2023, 27 pages.
International Preliminary Report on Patentability for International Application No. PCT/US2022/043833 dated Mar. 28, 2024, 5 pages.
International Preliminary Report on Patentability for International Application No. PCT/US2022/045587 dated Apr. 11, 2024, 11 pages.
International Preliminary Report on Patentability for International Application No. PCT/US2022/077432 dated Apr. 11, 2024, 9 pages.
International Preliminary Report on Patentability for International Application No. PCT/US2023/079137 mailed May 22, 2025, 9 pages.
International Preliminary Report on Patentability for International Application No. PCT/US2024/010486 mailed Jul. 17, 2025, 7 pages.
International Search Report and Written Opinion for International Application No. PCT/IB2023/058939 dated Dec. 1, 2023, 11 pages.
International Search Report and Written Opinion for International Application No. PCT/US2022/042353, mailed on Dec. 8, 2022, 9 pages.
International Search Report and Written Opinion for International Application No. PCT/US2022/043833 dated Jan. 12, 2023, 13 pages.
International Search Report and Written Opinion for International Application No. PCT/US2022/045587 dated Feb. 1, 2023, 25 pages.
International Search Report and Written Opinion for International Application No. PCT/US2022/077432 dated Dec. 15, 2022, 14 pages.
International Search Report and Written Opinion for International Application No. PCT/US2022/082468, mailed on Jun. 6, 2023, 11 pages.
International Search Report and Written Opinion for International Application No. PCT/US2023/079137 dated Apr. 29, 2024, 11 pages.
International Search Report and Written Opinion for International Application No. PCT/US2023/086567, dated May 24, 2024, 11 pages.
International Search Report and Written Opinion for International Application No. PCT/US2024/010486 mailed May 17, 2024. 10 pages.
International Search Report and Written Opinion for International Application No. PCT/US2024/032949, mailed Nov. 26, 2024. 11 pages.
International Search Report and Written Opinion for International Application No. PCT/US2024/033081, dated Oct. 24, 2024, 14 pages.
International Search Report and Written Opinion for International Application No. PCT/US2024/036639, mailed Sep. 23, 2024, 11 pages.
International Search Report and Written Opinion for International Application No. PCT/US2024/054056, mailed Feb. 10, 2025, 18 pages.
International Search Report and Written Opinion for International Application No. PCT/US2024/061447, mailed Feb. 26, 2025, 10 pages.
Invitation to Pay Additional Fees for International Application No. PCT/US2023/086567, mailed Mar. 18, 2024. 2 pages.
Invitation to Pay Additional Fees for International Application No. PCT/US2024/010486 mailed Mar. 12, 2024, 2 pages.
Invitation to Pay Additional Fees for International Application No. PCT/US2024/032949, mailed Aug. 6, 2024, 2 pages.
Invitation to Pay Additional Fees for International Application No. PCT/US2024/033081, mailed Aug. 15, 2024, 3 pages.
Invitation to Pay Fee for International Application No. PCT/US2022/045587 dated Nov. 18, 2022, 3 pages.
Invitation to Pay for International Application No. PCT/US2022/082468 dated Mar. 16, 2023, 2 pages.
Jeppesen, U., et al., "Dose-dependent inhibition of CYP1A2, CYP2C19 and CYP2D6 by citalopram, fluoxetine, fluvoxamine and paroxetine." Eur J Clin Pharmacol (1996) 51: 73-78.
Johnson et al., "Effects of enantiomers of MDA, MDMA and related analogues on [3H] serotonin and [3H] dopamine release from superfused rat brain slices." Eur J Pharmacol. Dec. 16, 1986;132(2-3):269-76. doi: 10.1016/0014-2999(86)90615-1.
Kalant, Harold, "The pharmacology and toxicology of "ecstasy" (MDMA) and related drugs." CMAJ. Oct. 2, 2001; 165(7): 917-28.
Kalivas et al., "MDMA Elicits Behavioral and Neurochemical Sensitization in Rats." Neuropsychopharmacology vol. 18, pp. 469-479 (1998).
Kamilar-Britt and Bedi, "The prosocial effects of 3,4-methylenedioxymethamphetamine (MDMA): Controlled studies in humans and laboratory animals." Neurosci Biobehav Rev. Oct. 2015: 57: 433-46. doi: 10.1016/j.neubiorev.2015.08.016. Epub Sep. 25, 2015.
Kashdan, T. B. & McKnight, P. E., "The darker side of social anxiety: When aggressive impulsivity prevails over shy inhibition." Current Directions in Psychological Science. Feb. 2010;19(1):47-50.
Kilpatrick et al., "National estimates of exposure to traumatic events and PTSD prevalence using DSM-IV and DSM-5 criteria." J Trauma Stress. Oct. 2013;26(5):537-47. doi: 10.1002/jts.21848.
Kirilly, E, et al., "Acute and long-term effects of a single dose of MDMA on aggression in Dark Agouti rats." Int J Neuropsychopharmacol. Feb. 2006; 9(1): 63-76.
Kiyatkin, "Environmental Conditions Modulate Neurotoxic Effects of Psycho motor Stimulant Drugs of Abuse." Int Rev Neurobiol. 2012 ; 102: 147-171. doi:10.1016/B978-0-12-386986-9.00006-5.
Koenig and Hilber, "The Anti-Addiction Drug Ibogaine and the Heart: A Delicate Relation." Molecules 2015, 20, 2208-2228; doi:10.3390/molecules20022208.
Kolbrich et al., "Physiological and subjective responses to controlled oral 3, 4-methylenedioxymethamphetamine administration", Journal of Clinical Psychopharmacology (2008); 28(4): 432-440. doi:10.1097/JCP.0b013e31817ef470.
Kotlyar et al., "Inhibition of CYP2D6 Activity by Bupropion." J Clin Psychopharmacol. Jun. 2005; 25(3): 226-9. doi: 10.1097/01.jcp.0000162805.46453.e3.
Kozma, D., et al., "Optical resolution of N-methylamphetamine via diastereoisomeric salt formation with 2R,3R-O,O'-di-p-toluoyltartaric acid," Chirality, 1999, vol. 11, Issue 5-6, pp. 373-375.
Ladd, et al., "Improved synthesis of fluoroveratroles and fluorophenethylamines via organolithium reagents." Journal of Organic Chemistry, 1981, pp. 203-206.

(56) References Cited

OTHER PUBLICATIONS

Leapman et al., "Application of parallel recorded EELS to analysis of beam-sensitive organic compounds." Biomed. Eng. Instrum., Proceedings—Annual Meeting, Electron Microscopy Society of America, 1988, pp. 632-633.
Leapman et al., "Applications of electron energy loss spectroscopy in biology: detection of calcium and fluorine." Proceedings—Annual Meeting, Electron Microscopy Society of America, 1982, pp. 412-415.
Lettfuss et al. "Is behavioral sensitization to 3,4-methylenedioxymethamphetamine (MDMA) mediated in part by cholinergic receptors?" Behav Brain Res. May 1, 2013: 244: 116-9. doi: 10.1016/j.bbr.2013.01.033. Epub Feb. 1, 2013.
Levine et al. (editor), "Principles of Forensic Toxicology," Springer, Fifth Edition, 2020, 680 pages.
Lewis et al., "Synthesis of R-and S-MDMA via nucleophilic ring-opening of homochiral N-tosylaziridines", Jul. 12, 2023 (Jul. 12, 2023), Australian Journal of Chemistry, 76(5), pp. 299-310.
Llabres et al., "Molecular basis of the selective binding of MDMA enantiomers to the alpha4beta2 nicotinic receptor subtype: synthesis, pharmacological evaluation and mechanistic studies", European Journal of Medicinal Chemistry (2014); 81: 35-46; 28 pages with Supporting Information.
Lourenco et al., "Chiral separation of 3, 4-methylenedioxymethamphetamine (MDMA) enantiomers using batch chromatography with peak shaving recycling and its effects on oxidative stress status in rat liver." J Pharm Biomed Anal. Jan. 25, 2013:73:13-7. doi: 10.1016/j.jpba.2012.01.025. Epub Jan. 30, 2012.
Ly et al., "Psychedelics promote structural and functional neural plasticity." Cell Rep. Jun. 12, 2018; 23(11): 3170-3182. doi: 10.1016/j.celrep.2018.05.022.
Lyon et al., "3, 4-Methylenedioxymethamphetamine (MDMA): stereoselective interactions at brain 5-$HT_1$ and 5-$HT_2$ receptors." Psychopharmacology (1986); 88: 525-526. doi: 10.1007/BF00178519.
Madry et al., "Evaluation of drug incorporation into hair segments and nails by enantiomeric analysis following controlled single MDMA intakes." Anal Bioanal Chem. Jan. 2016; 408(2): 545-56. doi: 10.1007/s00216-015-9130-3. Epub Oct. 31, 2015.
Madsen et al., "A single psilocybin dose is associated with long-term increased mindfulness, preceded by a proportional change in neocortical 5-HT2A receptor binding." Eur Neuropsychopharmacol. Apr. 2020: 33: 71-80. doi: 10.1016/j.euroneuro.2020.02.001. Epub Mar. 4, 2020.
Martins, et al., "Simultaneous enantioselective determination of amphetamine and congeners in hair specimens by negative chemical ionization gas chromatography-mass spectrometry." J Chromatogr B Analyt Technol Biomed Life Sci. Oct. 15, 2005;825(1):57-62. doi: 10.1016/j.jchromb.2004.12.037. Epub Jan. 27, 2005.
Martins, et al., "Time-resolved hair analysis of MDMA enantiomers by GC/MS-NCI." Forensic Sci Int. Oct. 25, 2007;172(2-3):150-5. doi: 10.1016/j.forsciint.2007.01.008. Epub Feb. 14, 2007.
Mas et al., "Cardiovascular and neuroendocrine effects and pharmacokinetics of 3, 4-methylenedioxymethamphetamine in humans." J Pharmacol Exp Ther. Jul. 1999;290(1):136-45.
Matsushima et al., "Optical isomer analysis of 3, 4-methylenedioxyamphetamine analogues and their stereoselective disposition in rats." J Anal Toxicol. Jan.-Feb. 1998;22(1):33-9. doi: 10.1093/jat/22.1.33.
McEwen et al., "Stress Effects on Neuronal Structure: Hippocampus, Amygdala, and Prefrontal Cortex." Neuropsychopharmacology. Jan. 2016; 41(1): 3-23. doi: 10.1038/npp.2015.171. Epub Jun. 16, 2015.
Miczek, K., "A new test for aggression in rats without aversive stimulation: Differential effects of d-amphetamine and cocaine." Psychopharmacology (Berl). Feb. 28, 1979; 60(3): 253-9. doi: 10.1007/BF00426664.
Miksys, et al., "Human CYP2D6 and mouse CYP2Ds: organ distribution in a humanized mouse model." Drug Metab Dispos. Oct. 2005; 33(10): 1495-502. doi: 10.1124/dmd.105.005488. Epub Jul. 20, 2005.
Milhazes, et al., Electrochemical and spectroscopic characterisation of amphetamine-like drugs: Application to the screening of 3,4-methylenedioxymethamphetamine (MDMA) and its synthetic precursors, Analytica Chimica Acta, 2007, pp. 231-241.
Mitchell et al., "MDMA-assisted therapy for severe PTSD: a randomized, double-blind, placebo-controlled phase 3 study", Nature Medicine (2021); 27(6): 1025-1033. doi: 10.1038/s41591-021-01336-3. Epub May 10, 2021.
Mithoefer et al., "The safety and efficacy of±3, 4-methylenedioxymethamphetamine-assisted psychotherapy in subjects with chronic, treatment-resistant posttraumatic stress disorder: the first randomized controlled pilot study." Journal of psychopharmacology. Apr. 2011;25(4):439-452.
Multidisciplinary Association for Psychedelic Studies (MAPS), "A Manual for Adherence Ratings of MDMA-Assisted Therapy for Treatment of Posttraumatic Stress Disorder, Version 6." MAPS, Santa Cruz, CA, Aug. 2021, 52 pages.
Murnane, et al., Discriminative stimulus effects of psychostimulants and hallucinogens in S (+)-3, 4-methylenedioxymethamphetamine (MDMA) and R (−)-MDMA trained mice, Journal of Pharmacology and Experimental Therapeutics, Nov. 1, 2009, pp. 717-723.
Murnane et al., "Endocrine and neurochemical effects of 3, 4-methylenedioxymethamphetamine and its stereoisomers in rhesus monkeys", Journal of Pharmacology and Experimental Therapeutics (2010); 334(2): 642-650. doi: 10.1124/jpet.110.166595. Epub May 13, 2010.
Murnane, et al., "The neuropharmacology of prolactin secretion elicited by 3, 4-methylenedioxymethamphetamine ("ecstasy"): a concurrent microdialysis and plasma analysis study." Horm Behav. Feb. 2012; 61(2): 181-90. doi: 10.1016/j.yhbeh.2011.10.012. Epub Dec. 14, 2011.
Mustafa, et al., Review Paper: MDMA and the Brain: A Short Review on the Role of Neurotransmitters in Neurotoxicity, Basic and Clinical Neuroscience, 2020, pp. 381-388.
Nair et al., "Fully validated, multi-kilogram cGMP synthesis of Mdma", ACS Omega (2021); 7(1): 900-907. doi: 10.1021/acsomega.1c05520.
Nash et al., "Effect of the R (−) and S (+) isomers of MDA and MDMA on phosphotidyl inositol turnover in cultured cells expressing 5-HT2A or 5-HT2C receptors", Neuroscience Letters (1994); 177(1-2): 111-115. doi: 10.1016/0304-3940(94)90057-4.
National Center for Biotechnology Information, "1-(1,3-benzodioxol-5-yl)-N ,3-dimethylbuta n-2-amine; hydrochloride: Pubchem CID 90667266" Pubchem entry (online), pp. 1-9, Mar. 11, 2015; Retrieved on Dec. 2, 2024 from the Internet: [URL: https://pubc hem.ncbi.nlm.nih.gov/compound/90667266].
National Center for Biotechnology Information, "[1-[2-(3,4-Dimethoxyphenyl)ethyl] cycloprop yl] carbamic acid: Pubchem CID 150096163" Pubchem entry (online), pp. 1-7, Dec. 13, 2018; Retrieved on Dec. 2, 2024 from the Internet: [URL: https://pubchem.ncbi.nlm.nih.gov/compound/150096163];.
National Center for Biotechnology Information, "[1-[(3,4-Dimethoxyphenyl)methyl] cyclobutyl] carbamic acid: Pubchem CID 135313815" Pubchem entry (online), pp. 1-8, Dec. 15, 2018; Retrieved on Dec. 2, 2024 from the Internet: [URL: https://pubchem .ncbi.nlm.nih.gov/compound/135313815].
National Center for Biotechnology Information, "[2-(I,3-Benzodioxol-5-yl)-2-methylpropyl] carbamic acid: Pubchem CID 115171385" Pubchem entry (online), pp. 1-7, Jan. 29, 2016; Retrieved on Dec. 2, 2024 from the Internet: [URL: https://pubchem.ncbi .nlm.nih.gov/compound/115171385].
National Center for Biotechnology Information "2-(I,3-benzodioxol-5-yl)ethyl carbamothio ic S-acid: Pubchem CID 115170245" Pubchem entry (online), pp. 1-7, Jan. 29, 2016; Retrieved on Dec. 1, 2024 from the Internet: [URL: https://pubchem.ncbi.nlm.nih.gov/ compound/115170245].
National Center for Biotechnology Information, "Ethyl (2S)-3-(1,3-benzodioxol-5-yl)-2-[(2-methylpropan-2-yl)oxycarbonylamino] propanoate: Pubchem CID 57958894" Pubchem entry (online), pp.

(56) References Cited

OTHER PUBLICATIONS 1-9, Aug. 19, 2012; Retrieved on Dec. 2, 2024 from the Internet: [URL: https://pubchem.ncbi.nlm.nih.gov/compound/57958894].
National Center for Biotechnology Information, "Ethyl N-[1-chloro-2-(3,4-dimethoxyphenyl) ethyl]carbamate: Pubchem CID 89487151" Pubchem entry (online), pp. 1-8, Feb. 13, 2015; Retrieved on Dec. 2, 2024 from the Internet: [URL: https://pubchem.nc bi.nlm.nih.gov/compound/89487151].
National Center for Biotechnology Information, "Ethyl N-[2-(I,3-benzodioxol-5-yl)ethyl] carbamate: Pubchem CID 15229637" Pubchem entry (online), pp. 1-9, Feb. 9, 2007; Retrieved on Dec. 1, 2024 from the Internet: [URL: https://pubchem.ncbi.nlm. nih.gov/compound/15229637].
National Center for Biotechnology Information, "Mbdp hydrochloride: Pubchem CID 90667265" Pubchem entry (online), pp. 1-10, Mar. 11, 2015; Retrieved on Dec. 2, 2024 from the Internet: [URL: https://pubchem.ncbi.nlm.nih.gov/compound/90667265].
National Center for Biotechnology Information, "Methyl N-[2-(1 ,3-benzodioxol-5-yl) ethyl]carbamodithioate: Pubchem CID 44125045" Pubchem entry (online), pp. 1-8, Jul. 27, 2009; Retrieved on Dec. 1, 2024 [URL: https://pubchem.ncbi.nlm.nih.gov/compound/44125045].
National Center for Biotechnology Information, "Methyl N-[(2R)-I-(I,3-benzodioxol-5-yl)-3-chloropropan-2-yl]carbamate: Pubchem CID 166107066" Pubchem entry (online), pp. 1-7, Dec. 20, 2022; Retrieved on Dec. 2, 2024 from the Internet: [URL: https:// pubchem.ncbi.nlm.nih.gov/compound/166107066].
National Center for Biotechnology Information, "Methyl N-[I-(I ,3-benzodioxol-5-yl) propan- 2-yl]carbamate: Pubchem CID 168188536" Pubchem entry (online), pp. 1-9, May 30, 2023; Retrieved on Dec. 1, 2024 from the Internet: [URL: https://pubchem.ncbi.n lm.nih.gov/compound/168188536].
National Center for Biotechnology Information, N-Methyl-1-(3,4-methylenedioxyphenyl)-2-butananiine: Pubchem CID 124844 Pubchem entry (online), pp. 1-8, Jul. 19, 2005; Retrieved on Dec. 2, 2024 from the Internet: [URL: https://pubchem.ncbi.nlm.nih.gov/ compound/124844].
National Center for Biotechnology Information, N-Moc-MDMA: Pubchem CID 165361551 Pubchem entry (online), pp. 1-11, Oct. 11, 2022; Retrieved on Dec. 2, 2024 from the Internet: [URL: https://pubchem.ncbi.nlm.nih.gov/compound/165361 551].
National Center for Biotechnology Infonnation, "Methyl N-[(2S)-1-(1,3-benzodioxol-5-yl)-3-chloropropan-2-yl]carbamate: Pubchem CID 166107086" Pubchem entry (online), pp. 1-7, Dec. 20, 2022; Retrieved on Dec. 2, 2024 from the Internet: [URL: https:// pubchem.ncbi.nlm.nih.gov/compound/166107086].
National Center for Biotechnology Information, "Methyl N-[4-(3,4-dimethoxyphenyl) oxan-4-yl]carbamate: Pubchem CID 142770320" Pubchem entry (online), pp. 1-8, Dec. 7, 2019; Retrieved on Dec. 2, 2024 from the Internet: [URL: https://pubchem.ncbi.nlm.nih.gov/compound/142770320].
Navarro and Maldonado, "Behavioral profile of 3,4-methylenedioxy-methamphetamine (MDMA) in agonistic encounters between male mice." Prog Neuropsychopharmacol Biol Psychiatry. Feb. 1999; 23(2): 327-34. doi: 10.1016/s0278-5846(98)00100-6.
Navarro and Maldonado, "Effects of acute, subchronic and intermittent MDMA ('Ecstasy') administration on agonistic interactions between male mice." Aggressive Behavior (2004) vol. 30, Issue 1, p. 84-91.
Nelson and Chiavegatto, "Molecular basis of aggression." Trends Neurosci. Dec. 2001; 24(12): 713-9. doi: 10.1016/s0166-2236(00)01996-2.
Nenajdenko et al., "A new convenient approach to chiral β-aryl (heteroaryl) alkylamines", Tetrahedron: Asymmetry (2001); 12(18): 2517-2527.
Neumann et al., "Aggression and anxiety: social context and neurobiological links, Front Behav Neurosci." Mar. 30, 2010: 4: 12. doi: 10.3389/fnbeh.2010.00012. eCollection 2010, 16 pages.
Nichols et al., "Derivatives of 1-(1, 3-benzodioxol-5-yl)-2-butanamine: representatives of a novel therapeutic class", Journal of Medicinal Chemistry (1986); 29(10): 2009-2015. doi: 10.1021/jm00160a035.
Nie, et al., "Synthesis of fluorodopamines: effect of aryl fluoro substituents on affinities for adrenergic and dopaminergic receptors." Medicinal Chemistry Research, Jan. 1996, pp. 318-332.
O'Mathuna, B., et al., "The Consequences of 3,4-Methylenedioxymethamphetamine Induced CYP2D6 Inhibition in Humans." J Clin Psychopharmacol. Oct. 2008; 28(5): 523-9. doi: 10.1097/JCP.0b013e318184ff6e.
Organic Chemistry Portal, Amino Protecting Groups, Stability, available online at: https://www.organic-chemistry.org/protectivegroups/amino.shtm, 1999, pp. 1-3.
Parrot, A C, "Is ecstasy MDMA? A review of the proportion of ecstasy tablets containing MDMA, their dosage levels, and the changing perceptions of purity." Psychopharmacology (Berl). May 2004; 173(3-4): 234-41. doi: 10.1007/s00213-003-1712-7. Epub Mar. 9, 2004.
Parrott AC, "Human psychopharmacology of Ecstasy (MDMA): a review of 15 years of empirical research." Hum Psychopharmacol. Dec. 2001; 16(8): 557-577.
Partial Supplementary European Search Report for European Application No. 22877438.6 mailed Jul. 7, 2025, 16 pages.
Peters. "Drug testing in blood: validated negative-ion chemical ionization gas chromatographic-mass spectrometric assay for enantioselective measurement of the designer drugs MDEA, MDMA, and MDA and its application to samples from a controlled study with MDMA", Clinical Chemistry (2005); 48(9); 1811-1822. doi: 10.1373/clinchem.2005.052746. Epub Aug. 11, 2005.
Peters, et al., Concentrations and ratios of amphetamine, methamphetamine, MDA, MDMA, and MDEA enantiomers determined in plasma samples from clinical toxicology and driving under the influence of drugs cases by GC-NICI-MS, Journal of Analytical Toxicology, Nov. 1, 2003, pp. 552-559.
Peters, et al., Drug testing in blood: validated negative-ion chemical ionization gas chromatographic-mass spectrometric assay for determination of amphetamine and methamphetamine enantiomers and its application to toxicology cases, Clinical Chemistry, Sep. 1, 2002, pp. 1472-1485.
Peters, et al., Negative-ion chemical ionization gas chromatography-mass spectrometry assay for enantioselective measurement of amphetamines in oral fluid: application to a controlled study with MDMA and driving under the influence cases, Clinical chemistry, Apr. 1, 2007 A, pp. 702-710.
Pitts et al., "3, 4-Methylenedioxymethamphetamine increases affiliative behaviors in squirrel monkeys in a serotonin 2A receptor-dependent manner." Neuropsychopharmacology (2017); 42(10): 1962-1971. doi: 10.1038/npp.2017.80. Epub Apr. 20, 2017.
Pitts et al., "(±)-MDMA and its enantiomers: potential therapeutic advantages of R(−)-MDMA." Psychopharmacology (2018); 235: 377-392. doi: 10.1007/s00213-017-4812-5. Epub Dec. 16, 2017.
Pizarro et al., "Synthesis and capillary electrophoretic analysis of enantiomerically enriched reference standards of MDMA and its main metabolites", Bioorganic & Medicinal Chemistry (2002); 10(4): 1085-1092. doi: 10.1016/s0968-0896(01)00367-4.
Pizarro. "Stereochemical analysis of 3, 4-methylenedioxymethamphetamine and its main metabolites in human samples including the catechol-type metabolite (3, 4-dihydroxymethamphetamine)", Drug Metabolism and Disposition (2004); 32(9): 1001-1007.
Pizzaro et al., "Determination of MDMA and its Metabolites in Blood and Urine by Gas Chromatography-Mass Spectrometry and Analysis of Enantiomers by Capillary Electrophoresis." J Anal Toxicol. Apr. 2002; 26(3): 157-65. doi: 10.1093/jat/26.3.157.
Pokorny et al., "Effect of Psilocybin on Empathy and Moral Decision-Making." International Journal of Neuropsychopharmacology (2017) 20(9): 747-757.
Pubchem 297429685 deposited on Jan. 27 (Jan. 27, 2016) p. 1-5. 2, structure.
Pubchem 459067002 deposited on Dec. 20, 2021 (Dec. 20, 2021) p. 1-5.
Pubchem, SID 235735835, Feb. 13, 2015, 8 pages.

(56) References Cited

OTHER PUBLICATIONS

Pubchem, SID 243280603, Modify Date: Jun. 24, 2015 [retrieved on Dec. 27, 2022, 7 pages. Retrieved: https://pubchem.ncbi.nlm.nih.gov/substance/243280603].
Pubchem, Substance Record for SID 104098418, Jan. 2011, 6 pages.
PubChem, Substance Record for SID 117678335, Apr. 2011, 6 pages.
Pubchem, Substance Record for SID 38492237, Dec. 5, 2007, 5 pages.
Pubchem, Substance Record for SID 406789554, Jul. 18, 2020, 6 pages.
Pubchem, Substance Record for SID 439624087, Jan. 15, 2021, 6 pages.
Pubill et al., "Neuronal nicotinic receptors as new targets for amphetamine-induced oxidative damage and neurotoxicity." Pharmaceuticals. 2011; 4(6):822-847. https://doi.org/10.3390/ph4060822.
Rasmussen et al., "Chiral separation and quantification of R/S-amphetamine, R/S-methamphetamine, R/S-MDA, R/S-MDMA, and R/S-MDEA in whole blood by GC-EI-MS," Journal of Chromatography B, (2006) 842: 136-141.
Rickli et al., "Pharmacological profile of novel psychoactive benzofurans", British Journal of Pharmacology (2015); 172(13): 3412-3425. doi: 10.1111/bph.13128. Epub Apr. 24, 2015.
Rothman et al., "Amphetamine-type central nervous system stimulants release norepinephrine more potently than they release dopamine and serotonin", Synapse. Jan. 2001; 39(1): 32-41.
Rudnick et al., 'The molecular mechanism of "ecstasy" [3, 4-methylenedioxy-methamphetamine (MDMA)]: serotonin transporters are targets for MDMA-induced serotonin release.' Proc. Natl. Acad. Sci. USA, vol. 89, pp. 1817-1821, Mar. 1992.
Saez-Briones and Hernandez, "MDMA (3,4-Methylenedioxymethamphetamine) Analogues as Tools to Characterize MDMA-Like Effects: An Approach to Understand Entactogen Pharmacology." Curr Neuropharmacol. Sep. 2013; 11(5): 521-34. doi: 10.2174/1570159X11311050007.
Sager et al., "In vitro to in vivo extrapolation of the complex drug-drug interaction of bupropion and its metabolites with CYP2D6; simultaneous reversible inhibition and CYP2D6 downregulation." Biochem Pharmacol. Jan. 1, 2017: 123: 85-96. doi: 10.1016/j.bcp.2016.11.007. Epub Nov. 9, 2016.
Sakai et al., "Novel Optical Resolution Technologies." Topics in Current Chemistry, 269, Springer, 2007, p. 1-313.
Sandtner et al., "Binding Mode Selection Determines the Action of Ecstasy Homologs at Monoamine Transporters." Mol Pharmacol. Jan. 2016; 89(1): 165-75. doi:10.1124/mol.115.101394. Epub Oct. 30, 2015.
Schenk and Bradbury, "Persistent sensitisation to the locomotor activating effects of MDMA following MDMA self-administration in rats." Pharmacol Biochem Behav. May 2015: 132: 103-107. doi: 10.1016/j.pbb.2015.03.001. Epub Mar. 8, 2015.
Schmid et al., "Acute subjective effects in LSD-and MDMA-assisted psychotherapy", Journal of Psychopharmacology (2021); 35(4): 362-374. doi: 10.1177/0269881120959604. Epub Oct. 8, 2020.
Schwaninger, et al., "Development and validation of LC-HRMS and GC-NICI-MS methods for stereoselective determination of MDMA and its phase I and II metabolites in human urine." Journal of Mass Spectrometry, Jul. 2011, pp. 603-614.
Schwaninger, et al., "Stereoselective urinary MDMA (ecstasy) and metabolites excretion kinetics following controlled MDMA administration to humans." Biochem Pharmacol. Jan. 1, 2012; 83(1): 131-8. doi: 10.1016/j.bcp.2011.09.023. Epub Sep. 29, 2011.
Segura, M., et al., "Contribution of cytochrome P450 2D6 to 3,4-methylenedioxymethamphetamine disposition in humans: use of paroxetine as a metabolic inhibitor probe." Clin Pharmacokinet. 2005; 44(6): 649-60. doi: 10.2165/00003088-200544060-00006.
Setola, et al., 3, 4-methylenedioxymethamphetamine (MDMA, "Ecstasy") induces fenfluramine-like proliferative actions on human cardiac valvular interstitial cells in vitro, Molecular Pharmacology, Jun. 1, 2003, pp. 1223-1229.
Simmler et al. Pharmacological characterization of designer cathinones in vitro. British Journal of Pharmacology. Jan. 2013; 168(2):458-470. doi: 10.1111/j.1476-5381.2012.02145.x.
Spanos and Yamamoto, "Acute and subchronic effects of methylenedioxymethamphetamine [(+/−)MDMA] on locomotion and serotonin syndrome behavior in the rat." Pharmacol Biochem Behav. Apr. 1989; 32(4): 835-40. doi: 10.1016/0091-3057(89)90044-0.
Steele, et al., "Stereochemical effects of 3, 4-methylenedioxymethamphetamine (MDMA) and related amphetamine derivatives on inhibition of uptake of [3H] monoamines into synaptosomes from different regions of rat brain." Biochemical Pharmacology, Jul. 15, 1987, pp. 2297-2303.
Steuer et al., "Impact of cytochrome P450 2D6 function on the chiral blood plasma pharmacokinetics of 3, 4-methylenedioxymethamphetamine (MDMA) and its phase I and II metabolites in humans", PloS One (2016); 11(3): e0150955; 19 pages. doi: 10.1371/journal.pone.0150955.
Strajhar et al., "Effects of lisdexamfetamine on plasma steroid concentrations compared with d-amphetamine in healthy subjects: A randomized, double-blind, placebo-controlled study." J Steroid Biochem Mol Biol. Feb. 2019: 186: 212-225. doi: 10.1016/j.jsbmb.2018.10.016. Epub Oct. 28, 2018.
Straumann, I., et al., "Acute effects of R-MDMA, S-MDMA, and racemic MDMA in a randomized double-blind cross-over trial in healthy participants." Neuropsychopharmacology. Dec. 2024; 50(2): 362-371. doi: 10.1038/s41386-024-01972-6. Epub Aug. 23, 2024.
Sun, et al., Facile and universal immobilization of L-lysine inspired by mussels, J. Mater. Chem., 2012, Journal of Materials Chemistry, 2012, pp. 10035-10041.
Thomas, et al., "Characterization of 3, 4-methylenedioxypyrovalerone discrimination in female Sprague-Dawley rats." Behavioural Pharmacology, Jul. 2021, pp. 524-532.
Thomas et al., "Psilocybin and Ketamine Acutely Promote Wakefulness, Suppress REM Sleep but Differentially Modulate High Frequency EEG Oscillatory Power in Wistar Kyoto Rats—a Preliminary Analysis." ACNP 59th Annual Meeting: Poster Session I, Neuropsychopharmacology. Dec. 2020;45(Suppl 1):68-169. M140, doi: 10.1038/s41386-020-00890-7, 1 page.
Thomsen, et al., "In Vitro Drug Metabolism by Human Carboxylesterase 1: Focus on Angiotensin-Converting Enzyme Inhibitors." Drug Metab Dispos. Jan. 2014; 42(1): 126-33. doi: 10.1124/dmd.113.053512. Epub Oct. 18, 2013.
Torner, L., "Actions of Prolactin in the Brain: From Physiological Adaptations to Stress and Neurogenesis to Psychopathology." Front Endocrinol (Lausanne). Mar. 30, 2016: 7: 25. doi: 10.3389/fendo.2016.00025. eCollection 2016. 6 pages.
Tournier, et al., Interaction of drugs of abuse and maintenance treatments with human P-glycoprotein (ABCB1) and breast cancer resistance protein (ABCG2), International Journal of Neuropsychopharmacology, Aug. 1, 2010, pp. 905-915.
Traynor, J.M., et al., "MDMA-Assisted Psychotherapy for BorderlinePersonality Disorder". Focus, 2022, 20(4):358-67, (focus.psychiatryonline.org).
U.S. Appl. No. 19/145,450, filed Jul. 2, 2025, by Gibbs et al.
Verrico et al., "MDMA (Ecstasy) and human dopamine, norepinephrine, and serotonin transporters: implications for MDMA-induced neurotoxicity and treatment." Psychopharmacology. Jan. 2007;189(4):489-503. doi: 10.1007/s00213-005-0174-5.
Verweij, A., "Impurities in illicit drug preparations; 3,4-methylenedioxyamphetamine and 3-4-methylenedioxymethylamphetamine." Forensic Sci Rev. Dec. 1992;4(2):137-46.
Weinstock, et al., "Synthesis and renal vasodilator activity of some dopamine agonist 1-aryl-2,3,4,5-tetrahydro-1H-3-benzazepine-7,8-diols: halogen and methyl analogs of fenoldopam." J Med Chem. Nov. 1986; 29(11): 2315-25. doi: 10.1021/jm00161a029.

(56) References Cited

OTHER PUBLICATIONS

Willins and Meltzer, "Direct injection of 5-HT2A receptor agonists into the medial prefrontal cortex produces a head-twitch response in rats." J Pharmacol Exp Ther. Aug. 1997; 282(2): 699-706.
Winstock, et al., "Ecstasy pill testing: harm minimization gone too far?" Addiction, 2001, pp. 1139-1148.
Wu, et al., "Estimation of tamoxifen metabolite concentrations in the blood of breast cancer patients through CYP2D6 genotype activity score." Breast Cancer Res Treat. Jun. 2012; 133(2): 677-83. doi: 10.1007/s10549-012-1963-2.
Young et al., "MDMA (N-methyl-3, 4-methylenedioxyamphetamine) and its stereoisomers: Similarities and differences in behavioral effects in an automated activity apparatus in mice", Pharmacology Biochemistry and Behavior (2008); 88(3): 318-331. doi: 10.1016/j.pbb.2007.09.002. Epub Sep. 14, 2007.
Young, M.B., et al., "3,4-Methylenedioxymethamphetamine facilitates fear extinction learning", Transl Psychiatry. Sep. 15, 2015; 5(9): e634. 8 pages.
Yubero-Lahoz et al., "Changes in CYP1A2 Activity in Humans after 3,4-Methylenedioxymethamphetamine (MDMA, Ecstasy) Administration Using Caffeine as a Probe Drug." Drug Metab. Pharmacokinet. 27 (6): 605-613 (2012).
Zapata-Torres et al., "Quantum-chemical, NMR and X-ray diffraction studies on (±)-1-[3, 4-(methylenedioxy) phenyl]-2-methylaminopropane", Journal of Molecular Graphics and Modelling (2008); 26(8): 1296-1305.
Bachlinksi et al., "MDMA (3,4-methylenedioxymethamphetamine) nitrate—an atypical salt form or a new trend in the drug market" Issues of Forensic Science 296: 86-84, Jan. 2017, DOI:10.34836/pk.2017.296.5, (9 pages).
Banasr et al., "Cell atrophy and loss in depression: reversal by antidepressant treatment," Curr Opin Cell Biol. Dec. 2011; 23(6): 730-7. doi: 10.1016/j.ceb.2011.09.002. Epub Oct. 11, 2011.
Basak et al., "Organometallic Reagents," in Organometallic Compounds: Synthesis, Reactions, and Applications, First Ed, eds Dakeshwar et al., Wiley-VCH GmbH, 2023, 267-300, (34 pages).
Bird et al., "Psilocybin and MDMA for the treatment of trauma-related psychopathology," Int Rev Psychiatry. May 2021; 33(3): 229-249. doi: 10.1080/09540261.2021.1919062. Epub Jun. 14, 2021.
CAS Registry, CAS RN 3048205-90-6, "1,3-Benzodioxole-5-ethanamine, N,α-dimethyl-, (αR)-, compd. with nitrate (1:1)," [chemical database], Chemical Abstracts Service, Columbus, OH, entered into STN International on Jul. 22, 2024. [Accessed Jun. 17, 2026, publicly available at URL: https://www.cas.org], 1 page.
EP Application No. 22870763.4, Extended European Search Report mailed Nov. 13, 2025; ATAI Life Sciences AG; 8 pages.
EP Application No. 22917528.6, Extended European Search Report mailed Nov. 24, 2025; Applicant EmpathBio, Inc; 8 pages.
Larranaga et al., "Organometallic Compound," in Hawley's Condensed Chemical Dictionary, Eds. Larranaga et al., 16th ed., John Wiley & Sons, Inc., Hoboken, New Jersey, 2016, p. 1014, (4 printed pages).
Law et al., "Organometallic compound," in a Dictionary of Chemistry, Eds. Law et al., 8th ed., Oxford University Press, 2020, pp. 413-414.
Law et al., "Reagent," in a Dictionary of Chemistry, Eds. Law et al., 8th ed., Oxford University Press, 2020, p. 485, (3 printed pages).
Morimoto et al., "Organic Compounds," Acta Crystallographica Section C54, Feb. 1998, pp. 229-231.
PCT Application No. PCT/US2024/033081, International Preliminary Report on Patentability mailed Dec. 18, 2025; Applicant Empathbio, Inc.; 9 pages.
PCT Application No. PCT/US2024/036639, International Preliminary Report on Patentability mailed Jan. 15, 2026, Applicant Empathbio, Inc.; 8 pages.
PCT Application No. PCT/US2024/054056, International Preliminary Report on Patentability mailed May 15, 2026, Applicant Empathbio Inc.; 14 pages.
Plotka et al., "Common methods for the chiral determination of amphetamine and related compounds I. Gas, liquid and thin-layer chromatography," TrAC Trends in Analytical Chemistry, (Jul. 2011), 30(7): 1139-1158, DOI:10.1016/j.trac.2011.03.013.
U.S. Appl. No. 19/431,012, filed Dec. 23, 2025, Inventor: Fawaz, Majed et al.
U.S. Appl. No. 19/498,923, filed Jan. 2, 2026, Inventor: Short, Glenn et al.
U.S. Appl. No. 19/644,615, filed Apr. 10, 2026, Inventor: Rao et al.
U.S. Appl. No. 19/704,761, filed Jun. 11, 2026, Inventor: Short et al.

SYNTHESIS OF MDA OR ITS OPTICALLY ACTIVE (R)- OR (S)-MDA ISOMERS

BACKGROUND

MDA (3,4-methylenedioxyamphetamine) is considered the prototype of a class of compounds called entactogens, which means "to touch within", their main characteristic being their ability to increase feelings of love, empathy and closeness towards others. Structurally, MDA is a ring-substituted phenethylamine with a chiral molecular center that gives rise to two stereoisomers: S-(+)-MDA and R-(−)-MDA. Typically, effects of the former resemble those of psychostimulants and are primarily mediated by dopaminergic and noradrenergic pathways, including increases in motor activity and euphoria, whereas the latter induces qualitative effects similar to classical psychedelics, such as ego-dissolution and perceptive alterations, mediated by serotonergic pathways, including direct 5-HT2A receptor agonism. The molecular mechanisms for these differences are supported by preclinical evidence and point to a higher therapeutic index for the R-enantiomer.

There remains a need for improved processes of making MDA (3,4-methylenedioxyamphetamine) and pharmaceutically acceptable salts thereof and enantiomers thereof.

SUMMARY

In an aspect, the present disclosure provides a process for the preparation of 3,4-methylenedioxyamphetamine (MDA). In some embodiments, the present disclosure provides a process for the preparation of racemic 3,4-methylenedioxyamphetamine (MDA). In some embodiments, the present disclosure provides a process for the preparation of enantiopure (R) or (S) 3,4-methylenedioxyamphetamine (MDA).

In embodiments, the present disclosure provides: a process for the preparation of 3,4-methylenedioxyamphetamine, or a pharmaceutically acceptable salt thereof, the process comprising:

i) reacting an organometallic reagent prepared from a compound of Formula (I):

(I)

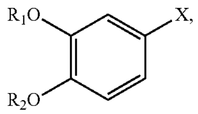

with a compound of Formula (IIb):

(IIb)

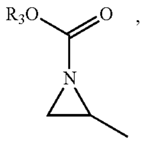

wherein $R_3$ is alkyl; and ii) converting the product of step i) to 3,4-methylenedioxyamphetamine, wherein X is a halogen; $R_1$ is a protecting group, $R_2$ is a protecting group or $R_1$ and $R_2$ together with the atoms to which they are attached form a 5-membered heterocycle.

In embodiments, the compound of Formula (IIb) is racemic.

In embodiments, the present disclosure provides: a process for the preparation of (S)-3,4-methylenedioxyamphetamine, or a pharmaceutically acceptable salt thereof, the process comprising:

i) reacting an organometallic reagent prepared from a compound of Formula (I):

(I)

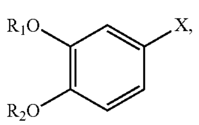

with a compound of Formula (II):

(II)

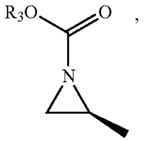

wherein $R_3$ is alkyl; and ii) converting the product of step i) to (S)-3,4-methylenedioxyamphetamine wherein X is a halogen; $R_1$ is a protecting group, $R_2$ is a protecting group or $R_1$ and $R_2$ together with the atoms to which they are attached form a 5-membered heterocycle.

In some embodiments, the present disclosure provides: a process for the preparation of (R)-3,4-methylenedioxyamphetamine, or a pharmaceutically acceptable salt thereof, the process comprising:

i) reacting an organometallic reagent prepared from a compound of Formula (I):

(I)

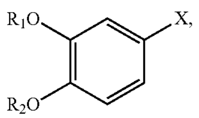

with a compound of Formula (IIa):

(IIa)

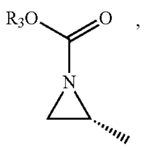

wherein $R_3$ is alkyl; and ii) converting the product of step ii) to (R)-3,4-methylenedioxyamphetamine, wherein X is a halogen; $R_1$ is a protecting group, $R_2$ is a protecting group or $R_1$ and $R_2$ together with the atoms to which they are attached form a 5-membered heterocycle.

In some embodiments, X is preferably bromine.

In some embodiments, the process provides 3,4-methylenedioxyamphetamine, or a pharmaceutically acceptable salt in as a racemate.

In some embodiments, the process provides (S)-3,4-methylenedioxyamphetamine, or a pharmaceutically acceptable salt in an enantiomeric excess of a least 99.5%.

In some embodiments, the process provides (R)-3,4-methylenedioxyamphetamine, or a pharmaceutically acceptable salt in an enantiomeric excess of a least 99.5%.

DETAILED DESCRIPTION

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The term “pharmaceutically acceptable salts” includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. The acids that may be used to prepare pharmaceutically acceptable acid addition salts of such basic compounds are those that form non-toxic acid addition salts, i.e., salts containing pharmaceutically acceptable anions, including but not limited to malate, oxalate, chloride, bromide, iodide, nitrate, acetate, tartrate, oleate, fumarate, formate, benzoate, glutamate, methanesulfonate, benzenesulfonate, and p-toluenesulfonate salts. Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine dicyclohexylamine and the like. Examples of metal salts include lithium, sodium, potassium, magnesium, calcium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Those skilled in the art will further recognize that acid addition salts may be prepared by reaction of the compounds with the appropriate inorganic or organic acid via any of a number of known methods.

When a range of values is listed, it is intended to encompass each value and sub-range within the range. For example, “$C_1$-$C_6$ alkyl” is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

“Alkyl” or “alkyl group” refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

“Heterocyclyl,” “heterocyclic ring” or “heterocycle” refers to a stable saturated, unsaturated, or aromatic 3- to 20-membered ring which consists of two to nineteen carbon atoms and from one to six heteroatoms selected from the group consisting of nitrogen, oxygen and sulfur, and which is attached to the rest of the molecule by a single bond. Heterocyclyl or heterocyclic rings include heteroaryls, heterocyclylalkyls, heterocyclylalkenyls, and hetercyclylalkynyls. Unless stated otherwise specifically in the specification, the heterocyclyl can be a monocyclic, bicyclic, tricyclic or tetracyclic ring system, which can include fused, bridged, or spirocyclic ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

The term “substituted” used herein means any of the groups described herein (e.g., alkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups.

"Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $—NR_gR_h$, $—NR_gC(═O)R_h$, $—NR_gC(═O)NR_gR_h$, $—NR_gC(═O)OR_h$, $—NR_gSO_2R_h$, $—OC(═O)NR_gR_h$, $—OR_g$, $—SR_g$, $—SOR_g$, $—SO_2R_g$, $—OSO_2R_g$, $—SO_2OR_g$, $═NSO_2R_g$, and $—SO_2NR_gR_h$. "Substituted" also means any of the above groups in which one or more hydrogen atoms are replaced with $—C(═O)R_g$, $—C(═O)OR_g$, $—C(═O)NR_gR_h$, $—CH_2SO_2R_g$, $—CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

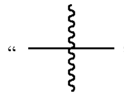

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

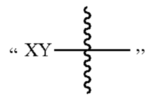

indicates that the chemical entity "XY" is bonded to another chemical entity via the point of attachment bond. Furthermore, the specific point of attachment to the non-depicted chemical entity can be specified by inference. For example, the compound $CH_3—R^{3X}$, wherein $R^{3X}$ is H or

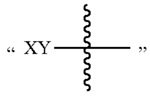

infers that when $R^{3X}$ is "XY", the point of attachment bond is the same bond as the bond by which $R^{3X}$ is depicted as being bonded to $CH_3$.

Methods

In an aspect, the methods described herein provide high purity, 3,4-methylenedioxyamphetamine (MDA) in a high yielding 2-step process, starting from readily available and inexpensive starting materials (e.g., 5-bromobenzo[d][1,3]dioxole (3) and alaninol). In an aspect, the disclosure provides a process for preparation of racemic 3,4-methylenedioxyamphetamine or a pharmaceutically acceptable salt thereof.

In an aspect, the disclosure provides a process for the preparation of (R)- or (S)-3,4-methylenedioxyamphetamine, or a pharmaceutically acceptable salt thereof.

In embodiments, the methods described herein provide high purity, enantiopure (R) or (S) 3,4-methylenedioxyamphetamine (MDA) in a high yielding 2-step process, starting from readily available and inexpensive starting materials (e.g., 5-bromobenzo[d][1,3]dioxole (3) and D-alaninol (1)). By starting with a chiral pool starting materials, such as (D-alaniol (1)), enantiopure (R)-MDA can be prepared without the need for expensive and wasteful chiral ligands, chiral auxiliaries, or diastereomeric salt resolutions, and provide MDA with higher optical purity (e.g., 99.5% ee or greater, or 99.9% ee) than other routes, which give lower selectivity and require enantiomeric enrichment by purification/crystallization. By installing a Boc group as a nitrogen protecting group, the reaction avoids the potential of over-alkylation and provides enantioenriched (R)-MDA in a streamlined process, providing significant improvements on prior syntheses which are more complex and/or require synthetic longer routes see e.g., *ACS Chem Neurosci.* 2018 Oct. 17; 9(10): 2408-2427, FIG. 3. The unnatural enantiomer of (1) (L-alaninol) can be used by the same process to prepare (S)-MDA.

Preparation of 3,4-Methylenedioxyamphetamine

In an aspect, the disclosure provides a process for the preparation of 3,4-methylenedioxyamphetamine, or a pharmaceutically acceptable salt thereof, the process comprising:

i) reacting an organometallic reagent prepared from a compound of Formula (I):

(I)

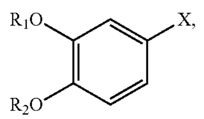

with a compound of Formula (IIb):

(IIb)

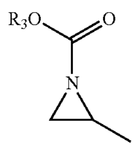

, wherein $R_3$ is alkyl; and ii) converting the product of step i) to 3,4-methylenedioxyamphetamine, wherein X is a halogen; $R_1$ is a protecting group, $R_2$ is a protecting group or $R_1$ and $R_2$ together with the atoms to which they are attached form a 5-membered heterocycle.

In embodiments, the compound of Formula (IIb) is a racemate.

In embodiments of the processes provided herein for the preparation of 3,4-methylenedioxyamphetamine, the process comprises i) preparing an organometallic reagent from a compound of Formula (I):

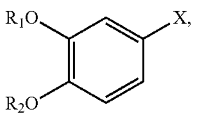
(I)

wherein X is a halogen; $R_1$ is a protecting group, $R_2$ is a protecting group or $R_1$ and $R_2$ together with the atoms to which they are attached form a 5-membered heterocycle.

In some embodiments of any one of the processes for the preparation of 3,4-methylenedioxyamphetamine described herein, $R_1$ and $R_2$ together with the atoms to which they are attached form a 5-membered heterocycle.

In some embodiments of the process for the preparation of 3,4-methylenedioxyamphetamine, the compound of Formula (I) is a compound of Formula (Ia):

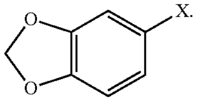
(Ia)

In embodiments of the compounds of Formula (I) or (Ia), X is Cl, Br, or I. In some embodiments, X is Cl. In some embodiments, X is Br. In some embodiments, X is I.

In some embodiments of the process for the preparation of 3,4-methylenedioxyamphetamine, step i) comprises reacting the compound of Formula (I) or Formula (Ia) with magnesium. In some embodiments, step i) comprises reacting the compound of Formula (I) or Formula (Ia) with magnesium in the presence of a solvent, for example an ether solvent such as tetrahydrofuran, diethyl ether, or 2-methyltetrahydrofuran. In some embodiments, the solvent is heated e.g., to 50-70° C., 60-70° C., or 60-66° C. In some embodiments, the solvent is heated to reflux. In some embodiments, the solvent is THF and the THF is heated to reflux.

In some embodiments of the process for the preparation of 3,4-methylenedioxyamphetamine, step i) further comprises adding a copper (I) salt (e.g., CuI, CuCl, or $CuBr{\cdot}SMe_2$) to the reaction mixture. In some embodiments, after formation of the Grignard species, the solution is cooled, and copper iodide (CuI) is added. In some embodiments, the solution is cooled for example, to a temperature between 0° C. and −78° C. and copper iodide (CuI) is added. In some embodiments, the organometallic reagent selectively opens the aziridine at the less hindered carbon, retaining the stereochemistry of the nitrogen stereocenter to give carbamate protected methylenedioxyamphetamine.

In embodiments of the process for the preparation of 3,4-methylenedioxyamphetamine, step i) comprises reacting the organometallic reagent of step i) with a compound of Formula (IIb):

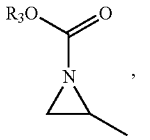
(IIb)

wherein $R_3$ is alkyl. In some embodiments, step i) comprises adding a compound of Formula (IIb) to the cooled solution of organometallic reagent.

In some embodiments of the process for the preparation of 3,4-methylenedioxyamphetamine, $R_3$ is $C_{1-6}$ alkyl. In some embodiments, $R_3$ is $C_{1-4}$ alkyl. In some embodiments, $R_3$ is tert-butyl.

In some embodiments of the process for the preparation of 3,4-methylenedioxyamphetamine, the product of step i) is a compound of Formula (IIIb):

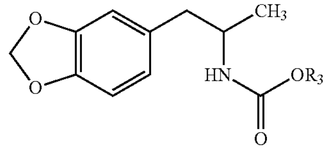
(IIIb)

wherein $R_3$ is defined herein.

In embodiments of the process for the preparation of 3,4-methylenedioxyamphetamine, the product of step i) is a compound of Formula (IIIc):

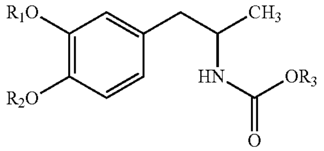
(IIIc)

wherein $R_1$, $R_2$, and $R_3$ are defined herein.

In some embodiments of the process for the preparation of 3,4-methylenedioxyamphetamine, step ii) comprises reacting a group of Formula (IVb) with a deprotecting agent to provide a group of Formula (Vb), or a pharmaceutically acceptable salt thereof:

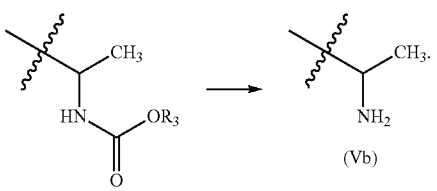
(IVb) (Vb)

In some embodiments, step ii) comprises reacting a group of Formula (IVb) with a deprotecting agent to provide a group of Formula (Vb), or a pharmaceutically acceptable salt thereof in the presence of a solvent, for example an ether solvent such as tetrahydrofuran, diethyl ether, 2-methyltetrahydrofuran. In some embodiments, the solvent is heated. In some embodiments, the solvent is refluxing THF.

In some embodiments of the process for the preparation of 3,4-methylenedioxyamphetamine, the deprotecting agent in step ii) is an acid. In some embodiments, the deprotecting agent in step ii) is hydrochloric acid.

In some embodiments of the process for the preparation of 3,4-methylenedioxyamphetamine, the process provides 3,4-methylenedioxyamphetamine, or a pharmaceutically acceptable salt thereof in racemic form.

In some embodiments of the process for the preparation of 3,4-methylenedioxyamphetamine, the 3,4-methylenedioxyamphetamine, or a pharmaceutically acceptable salt thereof has a chemical purity of greater than 95%, greater than 98%, or greater than 99% by HPLC.

In some embodiments, the present disclosure provides 3,4-methylenedioxyamphetamine, or a pharmaceutically acceptable salt prepared by a process described herein.

Preparation of (S)-3,4-Methylenedioxyamphetamine

In an aspect, the disclosure provides a process for the preparation of (S)-3,4-methylenedioxyamphetamine, or a pharmaceutically acceptable salt thereof, the process comprising:

i) reacting an organometallic reagent prepared from a compound of Formula (I):

(I)

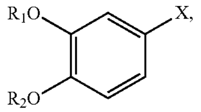

with a compound of Formula (II):

(II)

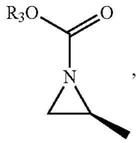

, wherein $R_3$ is alkyl; and ii) converting the product of step ii) to (S)-3,4-methylenedioxyamphetamine, wherein X is a halogen; $R_1$ is a protecting group, $R_2$ is a protecting group or $R_1$ and $R_2$ together with the atoms to which they are attached form a 5-membered heterocycle.

In embodiments of the processes provided herein for the preparation of (S)-3,4-methylenedioxyamphetamine, the process comprises preparing an organometallic reagent from a compound of Formula (I):

(I)

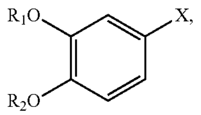

wherein X is a halogen; $R_1$ is a protecting group, $R_2$ is a protecting group or $R_1$ and $R_2$ together with the atoms to which they are attached form a 5-membered heterocycle.

In some embodiments of any one of the processes for the preparation of (S)-3,4-methylenedioxyamphetamine described herein, $R_1$ and $R_2$ together with the atoms to which they are attached form a 5-membered heterocycle.

In some embodiments of the process for the preparation of (S)-3,4-methylenedioxyamphetamine, the compound of Formula (I) is a compound of Formula (Ia):

(Ia)

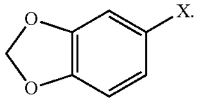

In embodiments of the compounds of Formula (I) or (Ia), X is Cl, Br, or I. In some embodiments, X is Cl. In some embodiments, X is Br. In some embodiments, X is I.

In some embodiments of the process for the preparation of (S)-3,4-methylenedioxyamphetamine, step i) comprises reacting the compound of Formula (I) or Formula (Ia) with magnesium. In some embodiments, step i) comprises reacting the compound of Formula (I) or Formula (Ia) with magnesium in the presence of a solvent, for example an ether solvent such as tetrahydrofuran, diethyl ether, 2-methyltetrahydrofuran. In some embodiments, the solvent is heated e.g., to 50-70° C., or 60-70° C., or 60-66° C. In some embodiments, the solvent is heated to reflux. In some embodiments, the solvent is THF and the THF is heated to reflux.

In some embodiments of the process for the preparation of (S)-3,4-methylenedioxyamphetamine, step i) further comprises adding a copper (I) salt (e.g., CuI, CuCl, $CuBr{\cdot}SMe_2$) to the reaction mixture. In some embodiments, after formation of the Grignard species, the solution is cooled, and copper iodide (CuI) is added. In some embodiments, the solution is cooled for example, to a temperature between 0° C. and −78° C. and copper iodide (CuI) is added. In some embodiments, the organometallic reagent selectively opens the aziridine at the less hindered carbon, retaining the stereochemistry of the nitrogen stereocenter to give carbamate protected methylenedioxyamphetamine.

In embodiments of the process for the preparation of (S)-3,4-methylenedioxyamphetamine, step i) further comprises reacting the organometallic reagent with a compound of Formula (II):

(II)

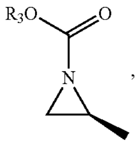

, wherein $R_3$ is alkyl. In some embodiments, step ii) comprises adding a compound of Formula (II) to the cooled solution of organometallic reagent.

In some embodiments of the process for the preparation of (S)-3,4-methylenedioxyamphetamine, $R_3$ is $C_{1-6}$ alkyl. In some embodiments, $R_3$ is $C_{1-4}$ alkyl. $R_3$ is tert-butyl.

In some embodiments of the process for the preparation of (S)-3,4-methylenedioxyamphetamine, the product of step i) is a compound of Formula (III):

(III)

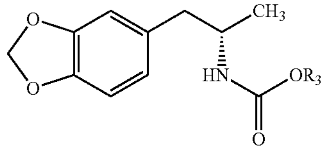

wherein $R_3$ is defined herein.

In some embodiments of the process for the preparation of (S)-3,4-methylenedioxyamphetamine, the product of step i) is a compound of Formula (IIIa):

(IIIa)

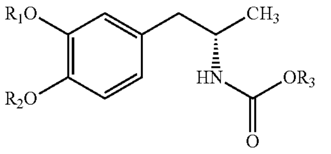

wherein $R_1$, $R_2$, and $R_3$ are defined herein.

In some embodiments of the process for the preparation of (S)-3,4-methylenedioxyamphetamine, step ii) comprises reacting a group of Formula (IV) with a deprotecting agent to provide a group of Formula (V), or a pharmaceutically acceptable salt thereof:

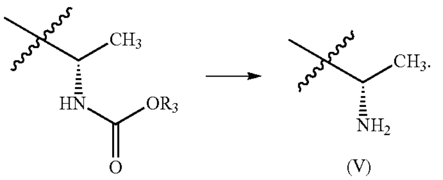

(IV) (V)

In some embodiments, step ii) comprises reacting a group of Formula (IV) with a deprotecting agent to provide a group of Formula (V), or a pharmaceutically acceptable salt thereof in the presence of a solvent, for example an ether solvent such as tetrahydrofuran, diethyl ether, 2-methyltetrahydrofuran. In some embodiments, the solvent is heated. In some embodiments, the solvent is refluxing THF.

In some embodiments of the process for the preparation of (S)-3,4-methylenedioxyamphetamine, the deprotecting agent in step ii) is an acid. In some embodiments, the deprotecting agent in step ii) is hydrochloric acid.

In some embodiments of the process for the preparation of (S)-3,4-methylenedioxyamphetamine, the process provides (S)-3,4-methylenedioxyamphetamine, or a pharmaceutically acceptable salt thereof in substantially optically pure form. In some embodiments, the process for the preparation of (S)-3,4-methylenedioxyamphetamine, the process provides (S)-3,4-methylenedioxyamphetamine, or a pharmaceutically acceptable salt in an enantiomeric excess (ee) of about or at least about 55% ee, about or at least about 60% ee, about or at least about 65% ee, about or at least about 70% ee, about or at 75% ee, about or at least about 80% ee, about or at least about 85% ee, about or at least about 90% ee, about or at least about 91%, about or at least about 92%, about or at least about 93% ee, about or at least about 94% ee, about or at least about 95% ee, about or at least about 96% ee, about or at least about 97% ee, about or at least about 98% ee, about or at least about 99% ee, about or at least about 99.5% ee, or about or at least about 99.9% ee, including all subranges and values therebetween. In some embodiments, the process for the preparation of (S)-3,4-methylenedioxyamphetamine, the process provides (S)-3,4-methylenedioxyamphetamine, or a pharmaceutically acceptable salt in an enantiomeric excess of a least 99.5%. In some embodiments, ee is measured by chiral HPLC.

In some embodiments of the process for the preparation of (S)-3,4-methylenedioxyamphetamine, the (S)-3,4-methylenedioxyamphetamine, or a pharmaceutically acceptable salt thereof has a chemical purity of greater than 95%, greater than 98%, or greater than 99% by HPLC.

In some embodiments, the present disclosure provides (S)-3,4-methylenedioxyamphetamine, or a pharmaceutically acceptable salt prepared by a process described herein.

Preparation of (R)-3,4-Methylenedioxyamphetamine

In an aspect, the disclosure provides a process or the preparation of (R)-3,4-methylenedioxyamphetamine, or a pharmaceutically acceptable salt thereof, the method comprising:

i) reacting an organometallic reagent prepared from a compound of Formula (I):

(I)

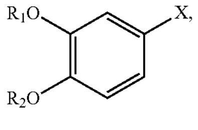

with a compound of Formula (IIa):

(IIa)

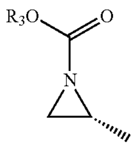

wherein $R_3$ is alkyl; and ii) converting the product of step ii) to (R)-3,4-methylenedioxyamphetamine, wherein X is a halogen; $R_1$ is a protecting group, $R_2$ is a protecting group or $R_1$ and $R_2$ together with the atoms to which they are attached form a 5-membered heterocycle.

In embodiments of the processes provided herein for the preparation of (R)-3,4-methylenedioxyamphetamine, the process comprises i) preparing an organometallic reagent from a compound of Formula (I):

(I)

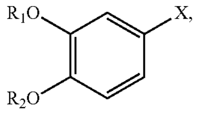

wherein X is a halogen; $R_1$ is a protecting group, $R_2$ is a protecting group or $R_1$ and $R_2$ together with the atoms to which they are attached form a 5-membered heterocycle.

In some embodiments of any one of the processes for the preparation of (R)-3,4-methylenedioxyamphetamine described herein, $R_1$ and $R_2$ together with the atoms to which they are attached form a 5-membered heterocycle.

In some embodiments of the process for the preparation of (R)-3,4-methylenedioxyamphetamine, the compound of Formula (I) is a compound of Formula (Ia):

(Ia)

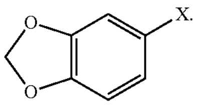

In embodiments of the compounds of Formula (I) or (Ia), X is Cl, Br, or I. In some embodiments, X is Cl. In some embodiments, X is Br. In some embodiments, X is I.

In some embodiments of the process for the preparation of (R)-3,4-methylenedioxyamphetamine, step i) comprises reacting the compound of Formula (I) or Formula (Ia) with magnesium. In some embodiments, step i) comprises reacting the compound of Formula (I) or Formula (Ia) with magnesium in the presence of a solvent, for example an ether solvent such as tetrahydrofuran, diethyl ether, 2-methyltetrahydrofuran. In some embodiments, the solvent is heated e.g., to 50-70° C. In some embodiments, the solvent is THF and the THF is heated to reflux.

In some embodiments of the process for the preparation of (R)-3,4-methylenedioxyamphetamine, step i) further comprises adding a copper (I) salt (e.g., CuI, CuCl, CuBr·$SMe_2$) to the reaction mixture. In some embodiments, after formation of the Grignard species, the solution is cooled, and copper iodide (CuI) is added. In some embodiments, the solution is cooled for example, to a temperature between 0° C. and −78° C. and copper iodide (CuI) is added. In some embodiments, the organometallic reagent selectively opens the aziridine at the less hindered carbon, retaining the stereochemistry of the nitrogen stereocenter to give carbamate protected methylenedioxyamphetamine.

In some embodiments of the process for the preparation of (R)-3,4-methylenedioxyamphetamine, comprises reacting the organometallic reagent with a compound of Formula (IIa):

(IIa)

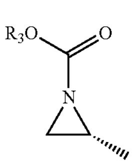

wherein $R_3$ is alkyl. In some embodiments, step ii) comprises adding a compound of Formula (IIa) to the cooled solution of organometallic reagent from step i).

In some embodiments of the process for the preparation of (R)-3,4-methylenedioxyamphetamine, $R_3$ is $C_{1-6}$ alkyl. In some embodiments, $R_3$ is $C_{1-4}$ alkyl. $R_3$ is tert-butyl.

In some embodiments of the process for the preparation of (R)-3,4-methylenedioxyamphetamine, the product of step i) is a compound of Formula (IIIb):

(IIIb)

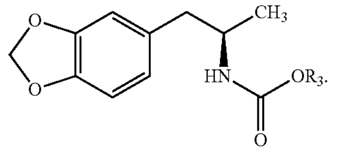

In some embodiments of the process for the preparation of (R)-3,4-methylenedioxyamphetamine, the product of step i) is a compound of Formula (IIIb'):

(IIIb')

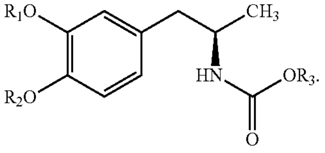

In some embodiments of the process for the preparation of (R)-3,4-methylenedioxyamphetamine, step ii) comprises reacting a group of Formula (IVa) with a deprotecting agent to provide a group of Formula (Va), or a pharmaceutically acceptable salt thereof:

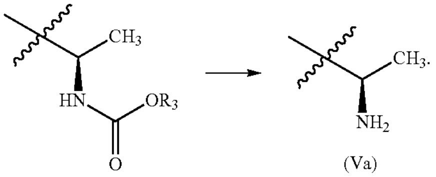

(IVa) (Va)

In some embodiments, step ii) comprises reacting a group of Formula (IV) with a deprotecting agent to provide a group of Formula (V), or a pharmaceutically acceptable salt thereof in the presence of a solvent, for example an ether solvent such as tetrahydrofuran, diethyl ether, 2-methyltetrahydrofuran.

In some embodiments of the process for the preparation of (R)-3,4-methylenedioxyamphetamine, the deprotecting agent in step ii) is an acid. In some embodiments, the deprotecting agent in step ii) is hydrochloric acid.

In some embodiments of the process for the preparation of (R)-3,4-methylenedioxyamphetamine, the process provides (R)-3,4-methylenedioxyamphetamine, or a pharmaceutically acceptable salt thereof in substantially optically pure form. In some embodiments, the process for the preparation of (R)-3,4-methylenedioxyamphetamine, the process provides (R)-3,4-methylenedioxyamphetamine, or a pharmaceutically acceptable salt in an enantiomeric excess (ee) of about or at least about 55% ee, about or at least about 60% ee, about or at least about 65% ee, about or at least about 70% ee, about or at 75% ee, about or at least about 80% ee, about or at least about 85% ee, about or at least about 90% ee, about or at least about 91%, about or at least about 92%, about or at least about 93% ee, about or at least about 94% ee, about or at least about 95% ee, about or at least about 96% ee, about or at least about 97% ee, about or at least about 98% ee, about or at least about 99% ee, about or at least about 99.5% ee, or about or at least about 99.9% ee, including all subranges and values therebetween. In some embodiments, the process for the preparation of (R)-3,4-methylenedioxyamphetamine, the process provides (R)-3,4-methylenedioxyamphetamine, or a pharmaceutically acceptable salt in an enantiomeric excess of a least 99.5%. In some embodiments, ee is measured by chiral HPLC.

In some embodiments of the process for the preparation of (R)-3,4-methylenedioxyamphetamine, the (R)-3,4-methylenedioxyamphetamine, or a pharmaceutically acceptable salt thereof has a chemical purity of greater than 95%, greater than 98%, or greater than 99% by HPLC.

In some embodiments, the present disclosure provides (R)-3,4-methylenedioxyamphetamine, or a pharmaceutically acceptable salt prepared by a process described herein.

Numbered Embodiments

1. A process for the preparation of (S)-3,4-methylenedioxyamphetamine, or a pharmaceutically acceptable salt thereof, the process comprising:

i) reacting an organometallic reagent prepared from a compound of Formula (I):

(I)

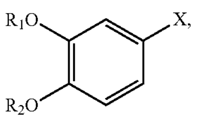

with a compound of Formula (II):

(II)

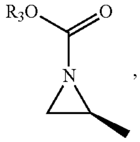

wherein $R_3$ is alkyl; and ii) converting the product of step ii) to (S)-3,4-methylenedioxyamphetamine, wherein X is a halogen; $R_1$ is a protecting group, $R_2$ is a protecting group or $R_1$ and $R_2$ together with the atoms to which they are attached form a 5-membered heterocycle.

2. The process of embodiment 1, wherein the compound of Formula (I) is a compound of Formula (Ia):

(Ia)

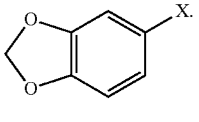

3. The process of embodiment 2, wherein X is bromine.

4. The process of any one of embodiments 1-3, wherein $R_3$ is tert-butyl.

5. The process of any one of embodiments 1-4, wherein step i) comprises reacting the compound of Formula (I) or Formula (Ia) with magnesium.

6. The process of embodiment 5, wherein the step i) further comprises adding a copper (I) salt (e.g., CuI) to the reaction mixture.

7. The process of any one of embodiments 1-6, wherein the product of step i) is a compound of Formula (III):

(III)

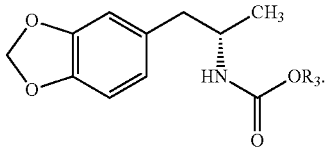

8. The process of any one of embodiments 1-6, wherein the product of step i) is a compound of Formula (IIIa):

(IIIa)

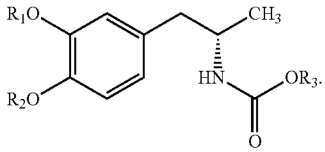

9. The process of any one of embodiments 1-8, wherein the step ii) comprises reacting a group of Formula (IV) with a deprotecting agent to provide a group of Formula (V), or a pharmaceutically acceptable salt thereof:

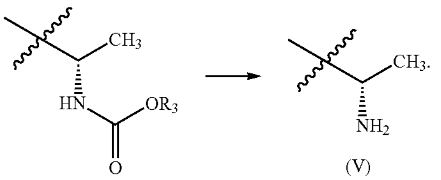

(IV) (V)

10. The process of embodiment 9, wherein the deprotecting agent is hydrochloric acid.

11. The process of any one of embodiments 1-10, wherein the process provides (S)-3,4-methylenedioxyamphetamine, or a pharmaceutically acceptable salt in an enantiomeric excess of a least 99.5%.

12. (S)-3,4-methylenedioxyamphetamine, or a pharmaceutically acceptable salt prepared by a process of any one of embodiments 1-10.

13. A process for the preparation of (R)-3,4-methylenedioxyamphetamine, or a pharmaceutically acceptable salt thereof, the process comprising:

i) reacting an organometallic reagent prepared from a compound of Formula (I):

(I)

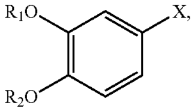

with a compound of Formula (IIa):

(IIa)

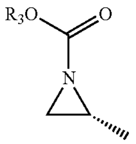

wherein $R_3$ is alkyl; and ii) converting the product of step ii) to (R)-3,4-methylenedioxyamphetamine, wherein X is a halogen; $R_1$ is a protecting group, $R_2$ is a protecting group or $R_1$ and $R_2$ together with the atoms to which they are attached form a 5-membered heterocycle.

14. The process of embodiment 13, wherein the compound of Formula (I) is a compound of Formula (Ia):

(Ia)

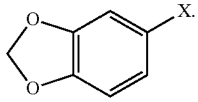

15. The process of any one of embodiments 13-14, wherein X is bromine.

16. The process of any one of embodiments 13-15, wherein $R_3$ is tert-butyl.

17. The process of any one of embodiments 13-16, wherein step i) comprises reacting the compound of Formula (I) or Formula (Ia) with magnesium.

18. The process of embodiment 17, wherein the step i) further comprises adding a copper (I) salt (e.g., CuI) to the reaction mixture.

19. The process of any one of embodiments 13-18, wherein the product of step i) is a compound of Formula (IIIb):

(IIIb)

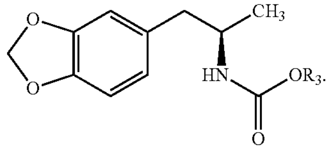

20. The process of any one of embodiments 13-18, wherein the product of step i) is a compound of Formula (IIIb'):

(IIIb')

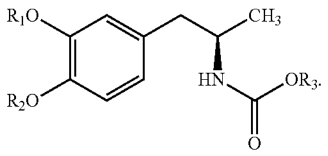

21. The process of any one of embodiments 13-20, wherein the step ii) comprises reacting a group of Formula (IVa) with a deprotecting agent to provide a group of Formula (Va), or a pharmaceutically acceptable salt thereof:

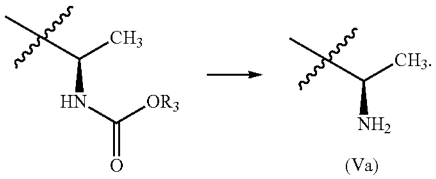

(Va)

(IVa)

22. The process of embodiment 21, wherein the deprotecting agent is hydrochloric acid.

23. The process of any one of embodiments 13-22, wherein the (R)-3,4-methylenedioxyamphetamine, or pharmaceutically acceptable salt is in an enantiomeric excess of a least 99.5%.

24. (R)-3,4-methylenedioxyamphetamine, or a pharmaceutically acceptable salt prepared by a process of any one of embodiments 13-23.

25. A process for the preparation of 3,4-methylenedioxyamphetamine, or a pharmaceutically acceptable salt thereof, the process comprising:

i) reacting an organometallic reagent prepared from a compound of Formula (I):

(I)

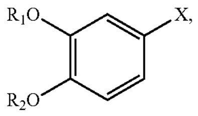

with a compound of Formula (II):

(IIb)

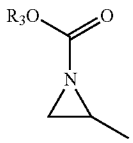
, wherein $R_3$ is alkyl; and ii) converting the product of step ii) to 3,4-methylenedioxyamphetamine, wherein X is a halogen; $R_1$ is a protecting group, $R_2$ is a protecting group or $R_1$ and $R_2$ together with the atoms to which they are attached form a 5-membered heterocycle.

26. The process of embodiment 25, wherein the compound of Formula (I) is a compound of Formula (Ia):

(Ia)

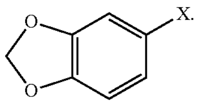

27. The process of embodiment 26, wherein X is bromine.

28. The process of any one of embodiments 25-27, wherein $R_3$ is tert-butyl.

29. The process of any one of embodiments 25-28, wherein step i) comprises reacting the compound of Formula (I) or Formula (Ia) with magnesium.

30. The process of embodiment 29, wherein the step i) further comprises adding a copper (I) salt (e.g., CuI) to the reaction mixture.

31. The process of any one of embodiments 25-30, wherein the product of step i) is a compound of Formula (III):

(IIIb)

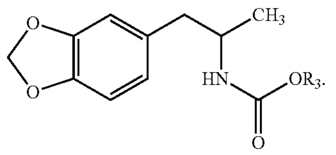

32. The process of any one of embodiments 25-30, wherein the product of step i) is a compound of Formula (IIIc):

(IIIc)

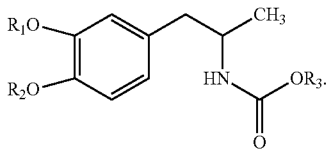

33. The process of any one of embodiments 1-8, wherein the step ii) comprises reacting a group of Formula (IVb) with a deprotecting agent to provide a group of Formula (Vb), or a pharmaceutically acceptable salt thereof:

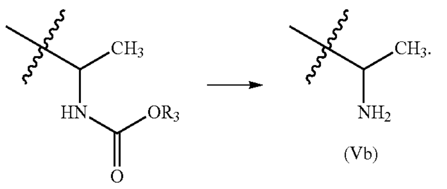

(IVb) (Vb)

34. The process of embodiment 33, wherein the deprotecting agent is hydrochloric acid.

35. The process of any one of embodiments 25-34, wherein the (S)-3,4-methylenedioxyamphetamine or pharmaceutically acceptable salt is in an enantiomeric excess of a least 99.5%.

36. 3,4-methylenedioxyamphetamine, or a pharmaceutically acceptable salt prepared by a process of any one of embodiments 25-35.

EXAMPLES

Compounds of the present disclosure are synthesized using the following exemplary methods or other methods that are known to those skilled in the art.

General reaction conditions are provided, and reaction products are purified by known methods including silica gel chromatography using various organic solvents such as hexane, dichloromethane, ethyl acetate, methanol and the like or preparative reverse phase high pressure liquid chromatography.

Preparation of compounds involves the protection and deprotection of various chemical groups. The need for protection and deprotection, and the selection of appropriate protecting groups is readily determined by one skilled in the art. The chemistry of protecting groups can be found, for example, in Greene and Wuts, *Protective Groups in Organic Synthesis,* 44th. Ed., Wiley & Sons, 2006, as well as in Jerry March, *Advanced Organic Chemistry,* $4^{th}$ edition, John Wiley & Sons, publisher, New York, 1992 which are incorporated herein by reference in their entirety.

General Synthesis of (R)-3,4-Methylenedioxyamphetamine (MDA)

(R)-3,4-methylenedioxyamphetamine (MDA) is synthesized according to Scheme 1, below.

Scheme 1

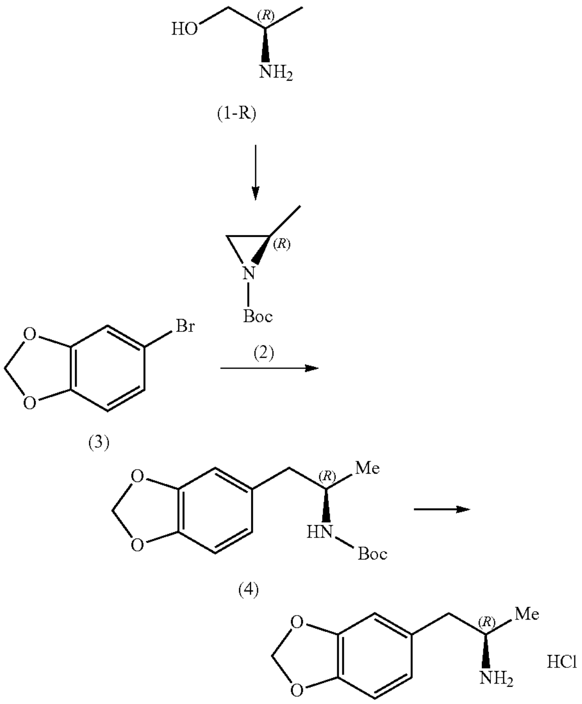

(1-R) (3) (2) (4) (R)-MDA

Step 1: Synthesis of tert-butyl (R)-2-methylaziridine-1-carboxylate (2)

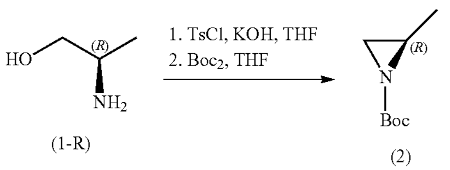

(1-R) (2)

To D-alaninol (1) is added 4-toluenesulfonyl chloride (TsCl), followed by potassium hydroxide (KOH), which installs the tosyl group on the alcohol and deprotonates the nitrogen, facilitating aziridine formation. The enantiopure aziridine intermediate is subsequently protected with di-tert-butyl dicarbonate (Boc anhydride) in organic solvent (e.g., halogenated solvent such as dichloromethane (DCM), either solvent such as tetrahydrofuran (THF) or methyl-tetrahydrofuran (Me-THF)) to form compound (2), which is then purified. In the scheme above, compound (2) may be synthesized as shown or it may be purchased since compound (2) is a commercially available compound.

Step 2: Synthesis of tert-butyl (R)-(1-(benzo[d][1,3]dioxol-5-yl)propan-2-yl)carbamate (4)

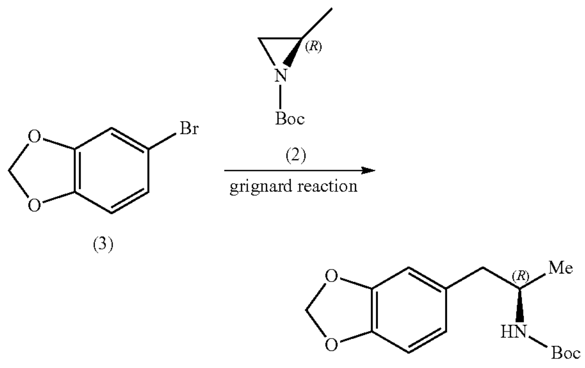

(2)

(3)

(4)

In a second step, the Grignard reagent of 5-bromobenzo[d][1,3]dioxole (3) is generated by treatment of 5-bromobenzo[d][1,3]dioxole (3) with magnesium, optionally in the presence of $I_2$, in organic solvent (e.g., ether solvent such as tetrahydrofuran (THF) or methyl-tetrahydrofuran (Me-THF)) and the mixture heated. After formation of the Grignard species, the solution is cooled and Copper (I) salt e.g., CuI or $CuBr{\cdot}SMe_2$ is added. The previously isolated Boc-aziridine (2) is then added to the cooled solution of cuprate and stirred until the reaction is complete. The reaction is then quenched with an aqueous solution e.g., with $NH_4Cl$ and the organic phase extracted with organic solvent and purified by chromatography on $SiO_2$, or by crystallization.

Step 3: Synthesis of (R)-3,4-Methylenedioxyamphetamine (MDA)

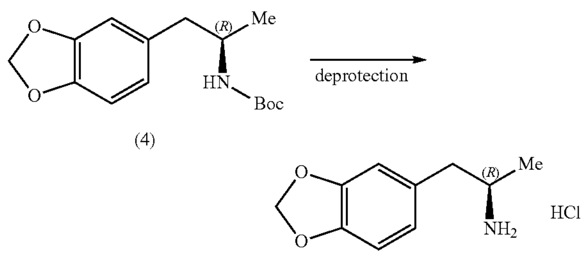

(4)

(R)-MDA

The Boc-MDA (4) is then dissolved in organic solvent (e.g., in an ether solvent such as tetrahydrofuran, (THF) or 2-methyltetrahydrofuran (Me-THF)). The Boc protecting group of compound (4) may be removed under strongly acidic conditions to generate the free amine.

(S)-3,4-methylenedioxyamphetamine (MDA) can be synthesized according to Scheme 1 employing L-alaninol instead of D-alaninol.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

The invention claimed is:

1. A process for the preparation of(S)-3,4-methylenedioxyamphetamine, or a pharmaceutically acceptable salt thereof, the process comprising:

i) reacting an organometallic reagent prepared from a compound of Formula (I):

(I)

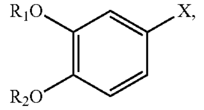

with a compound of Formula (II):

(II)

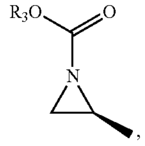

wherein $R_3$ is alkyl; and ii) converting the product of step i) to (S)-3,4-methylenedioxyamphetamine, wherein X is a halogen; $R_1$ is a protecting group, $R_2$ is a protecting group or $R_1$ and $R_2$ together with the atoms to which they are attached form a 5-membered heterocycle.

2. The process of claim 1, wherein the compound of Formula (I) is a compound of Formula (Ia):

(Ia)

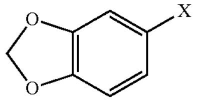

wherein the product of step i) is a compound of Formula (III):

(III)

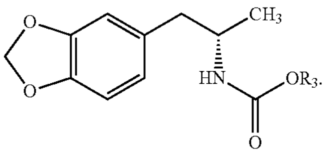

3. The process of claim 1, wherein X is bromine and $R_3$ is tert-butyl.

4. The process of claim 1, wherein step i) comprises reacting the compound of Formula (I) with magnesium.

5. The process of claim 4, wherein the step i) further comprises adding a copper (I) salt to the reaction mixture.

6. The process of claim 1, wherein the product of step i) is a compound of Formula (IIIa):

(IIIa)

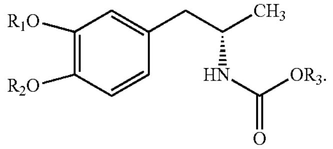

7. The process of claim 1, wherein the step ii) comprises reacting a group of Formula (IV) with a deprotecting agent to provide a group of Formula (V), or a pharmaceutically acceptable salt thereof:

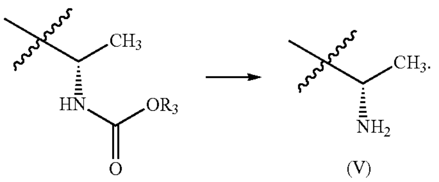

(IV) (V)

8. The process of claim 1, wherein the(S)-3,4-methylene-dioxyamphetamine, or pharmaceutically acceptable salt is in an enantiomeric excess of at least 99.5%.

9. A process for the preparation of (R)-3,4-methylenedi-oxyamphetamine, or a pharmaceutically acceptable salt thereof, comprising:

i) reacting an organometallic reagent prepared from a compound of Formula (I):

(I)

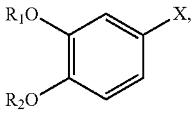

with a compound of Formula (IIa):

(IIa)

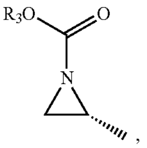

wherein $R_3$ is alkyl; and ii) converting the product of step i) to (R)-3,4-methylene-dioxyamphetamine, wherein X is a halogen; $R_1$ is a protecting group, $R_2$ is a protecting group or $R_1$ and $R_2$ together with the atoms to which they are attached form a 5-membered heterocycle.

10. The process of claim 9, wherein the compound of Formula (I) is a compound of Formula (Ia):

(Ia)

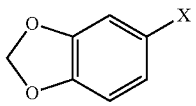

wherein the product of step i) is a compound of Formula (IIIb):

(IIIb)

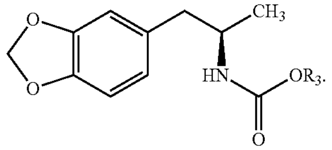

11. The process of claim 9, wherein X is bromine and $R_3$ is tert-butyl.

12. The process of claim 9, wherein step i) comprises reacting the compound of Formula (I) with magnesium.

13. The process of claim 12, wherein the step i) further comprises adding a copper (I) salt to the reaction mixture.

14. The process of claim 9, wherein the product of step i) is a compound of Formula (IIIb'):

(IIIb')

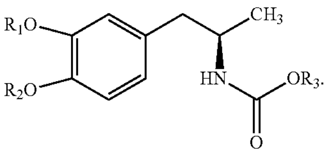

15. The process of claim 9, wherein the step ii) comprises reacting a group of Formula (IVa) with a deprotecting agent to provide a group of Formula (Va), or a pharmaceutically acceptable salt thereof:

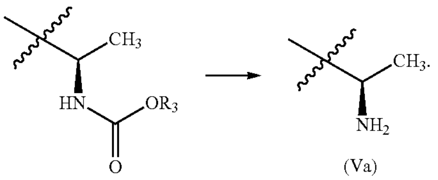

(IVa) (Va)

16. The process of claim 9, wherein the (R)-3,4-methyl-enedioxyamphetamine or pharmaceutically acceptable salt is in an enantiomeric excess of at least 99.5%.

17. A process for the preparation of 3,4-methylenedi-oxyamphetamine, or a pharmaceutically acceptable salt thereof, the process comprising:

i) reacting an organometallic reagent prepared from a compound of Formula (I):

(I)

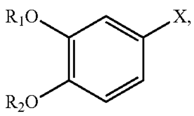

with a compound of Formula (IIb):

(IIb)

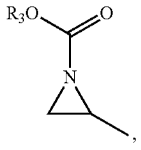

wherein $R_3$ is alkyl; and ii) converting the product of step i) to 3,4-methylenedioxyamphetamine, wherein X is a halogen; $R_1$ is a protecting group, $R_2$ is a protecting group or $R_1$ and $R_2$ together with the atoms to which they are attached form a 5-membered heterocycle.

18. The process of claim 17, wherein the product of step i) is a compound of Formula (IIIc):

(IIIc)

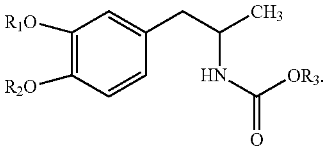

19. The process of claim 17, wherein the step ii) comprises reacting a group of Formula (IVb) with a deprotecting agent to provide a group of Formula (Vb), or a pharmaceutically acceptable salt thereof:

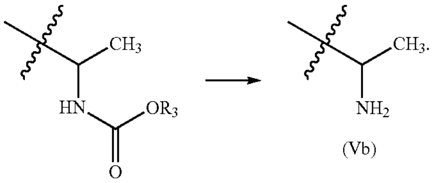

(Vb)

(IVb)

20. The process of claim 17, wherein the method produces 3,4-methylenedioxyamphetamine, or a pharmaceutically acceptable salt with a purity of at least 99%.

* * * * *